US012084610B2

United States Patent
South et al.

(10) Patent No.: US 12,084,610 B2
(45) Date of Patent: Sep. 10, 2024

(54) COMPOSITIONS AND METHODS FOR REDUCING DELETERIOUS ATMOSPHERIC GAS EMISSIONS FROM FLOODED ECOSYSTEMS

(71) Applicant: Arkea Bio Corp., Charlestown, MA (US)

(72) Inventors: Colin South, Reno, NV (US); Matthew Dunn, Louisville, CO (US); Caitlin Allen, Somerville, MA (US); Alexander Hsu, Belmont, MA (US); Sara Tabandeh, Cambridge, MA (US); Frederick Richard Kearney, Walpole, MA (US)

(73) Assignee: Arkea Bio Corp., Charlestown, MA (US)

( * ) Notice: Subject to any disclaimer, the term of this patent is extended or adjusted under 35 U.S.C. 154(b) by 0 days.

(21) Appl. No.: 18/217,227

(22) Filed: Jun. 30, 2023

(65) Prior Publication Data
US 2024/0002726 A1 Jan. 4, 2024

Related U.S. Application Data

(60) Provisional application No. 63/357,952, filed on Jul. 1, 2022.

(51) Int. Cl.
*C09K 17/50* (2006.01)
*B01D 51/04* (2006.01)
(Continued)

(52) U.S. Cl.
CPC ............ *C09K 17/50* (2013.01); *B01D 51/04* (2013.01); *B09C 1/08* (2013.01); *C02F 1/00* (2013.01);
(Continued)

(58) Field of Classification Search
CPC .... C09K 17/50; C09K 2101/00; B01D 51/04; B09C 1/08; C02F 1/00; C02F 1/68; C07C 205/00
(Continued)

(56) References Cited

U.S. PATENT DOCUMENTS 5,843,498 A 12/1998 Takahashi
6,036,950 A 3/2000 Baker
(Continued)

FOREIGN PATENT DOCUMENTS

AU 2011328948 B2 8/2016
AU 2013288441 B2 3/2017
(Continued)

OTHER PUBLICATIONS

Machine-generated English translation of CN 113710100, generated on Jan. 2, 2024.*
(Continued)

*Primary Examiner* — Fred Prince
(74) *Attorney, Agent, or Firm* — Foley Hoag LLP; Thi K. Dio; Hilary Dorr Lang

(57) ABSTRACT

The present disclosure provides compositions and methods for reducing emissions of deleterious atmospheric gases and/or precursors thereof from a flooded ecosystem comprising: one or more small molecules that reduce the production of one or more deleterious atmospheric gases and/or precursors thereof and one or more agriculturally suitable carriers.

25 Claims, 17 Drawing Sheets

(51) Int. Cl.
  *B09C 1/08* (2006.01)
  *C02F 1/00* (2023.01)
  *C02F 1/68* (2023.01)
  *C07C 205/00* (2006.01)
  *C09K 101/00* (2006.01)

(52) U.S. Cl.
  CPC .............. *C07C 205/00* (2013.01); *C02F 1/68* (2013.01); *C09K 2101/00* (2013.01); *Y02P 60/22* (2015.11)

(58) Field of Classification Search
  USPC ... 210/170.01, 170.02, 170.09, 170.1, 747.1, 210/747.5, 747.9, 749; 514/509
  See application file for complete search history.

(56) References Cited

U.S. PATENT DOCUMENTS

| | | |
|---|---|---|
| 6,251,879 B1 | 6/2001 | May et al. |
| 6,689,354 B2 | 2/2004 | Baker et al. |
| 7,763,273 B2 | 7/2010 | Losa |
| 7,820,171 B2 | 10/2010 | Maiti |
| 8,197,863 B2 | 6/2012 | Maye |
| 8,956,996 B2 | 2/2015 | Gewehr et al. |
| 8,969,419 B2 | 3/2015 | Garden et al. |
| 9,266,814 B2 | 2/2016 | Duval et al. |
| 9,365,489 B2 | 6/2016 | Duval et al. |
| 9,637,731 B2 | 5/2017 | Scalzi et al. |
| 9,902,685 B2 | 2/2018 | Duval et al. |
| 10,154,981 B2 | 12/2018 | Duval et al. |
| 10,440,975 B2 | 10/2019 | Park et al. |
| 10,500,236 B2 | 12/2019 | Sutherland et al. |
| 10,695,393 B2 | 6/2020 | McNeff et al. |
| 10,799,544 B2 | 10/2020 | Rintola et al. |
| 10,806,706 B2 | 10/2020 | Brunner et al. |
| 10,881,697 B2 | 1/2021 | Machado et al. |
| 10,961,559 B2 | 3/2021 | Mizrahi |
| 11,013,245 B2 | 5/2021 | Brunner et al. |
| 11,044,925 B2 | 6/2021 | Paternó |
| 11,191,288 B2 | 12/2021 | Duval et al. |
| 11,344,501 B2 | 5/2022 | Pimentel et al. |
| 11,529,310 B2 * | 12/2022 | Lay ..................... A61K 9/0068 |
| 2003/0003104 A1 | 1/2003 | Mottola et al. |
| 2003/0219467 A1 | 11/2003 | Miner et al. |
| 2012/0171323 A1 | 7/2012 | Bravo et al. |
| 2012/0276058 A1 | 11/2012 | Smith et al. |
| 2013/0011384 A1 | 1/2013 | Morgavi et al. |
| 2014/0072535 A1 | 3/2014 | Hatano et al. |
| 2014/0322798 A1 | 10/2014 | Scalzi et al. |
| 2014/0378412 A1 | 12/2014 | Lowe et al. |
| 2015/0064305 A1 | 3/2015 | Duval et al. |
| 2016/0183564 A1 | 6/2016 | Duval et al. |
| 2018/0001358 A1 | 1/2018 | Scalzi et al. |
| 2018/0093308 A1 | 4/2018 | Mueller et al. |
| 2019/0277833 A1 | 9/2019 | Gottlieb et al. |
| 2019/0343149 A1 | 11/2019 | Gadient et al. |
| 2020/0121730 A1 | 4/2020 | Mitteness |
| 2020/0138056 A1 | 5/2020 | Graz et al. |
| 2020/0155462 A1 | 5/2020 | Brunner et al. |
| 2021/0120844 A1 | 4/2021 | Riebel et al. |
| 2021/0163397 A1 | 6/2021 | Laeuger et al. |
| 2021/0227850 A1 | 7/2021 | O'Flaherty et al. |
| 2021/0267214 A1 | 9/2021 | Farmer et al. |
| 2021/0315952 A1 | 10/2021 | Farmer et al. |
| 2021/0360945 A1 | 11/2021 | King et al. |
| 2021/0392922 A1 | 12/2021 | Baati et al. |
| 2022/0015390 A1 | 1/2022 | Farmer et al. |
| 2022/0053798 A1 | 2/2022 | Vidoni et al. |
| 2022/0088110 A1 | 3/2022 | McNeff et al. |
| 2022/0175670 A1 | 6/2022 | Lay et al. |
| 2022/0192229 A1 | 6/2022 | Duval et al. |
| 2022/0256890 A1 | 8/2022 | Hafner et al. |
| 2023/0029570 A1 * | 2/2023 | Farmer ..................... C05F 11/02 |

FOREIGN PATENT DOCUMENTS

| | | |
|---|---|---|
| AU | 2018229465 A1 | 4/2019 |
| AU | 2015279261 B8 | 5/2019 |
| AU | 2018383221 A1 | 7/2020 |
| AU | 2020217418 B2 | 9/2022 |
| CN | 205662436 U * | 10/2016 |
| CN | 113710100 A * | 11/2021 |
| EP | 1673983 A1 | 6/2006 |
| EP | 2747181 A1 | 6/2014 |
| EP | 2838376 B1 | 4/2016 |
| EP | 3238720 A1 | 11/2017 |
| EP | 2969977 B1 | 12/2019 |
| EP | 3628169 A1 | 4/2020 |
| EP | 3849961 A1 | 7/2021 |
| NZ | 562783 A | 5/2010 |
| WO | WO-2007/072848 A1 | 6/2007 |
| WO | WO-2007/072935 A1 | 6/2007 |
| WO | WO-2010/071222 A1 | 6/2010 |
| WO | WO-2011/153299 A3 | 4/2012 |
| WO | WO-2012/084629 A1 | 6/2012 |
| WO | WO 2012/159186 A1 * | 11/2012 |
| WO | WO-2016/007173 A1 | 1/2016 |
| WO | WO-2017/137489 A1 | 8/2017 |
| WO | WO-2018/091643 A1 | 5/2018 |
| WO | WO-2018/149756 A1 | 8/2018 |
| WO | WO 2020/210074 A1 * | 10/2020 |
| WO | WO-2020/221805 A1 | 11/2020 |
| WO | WO-2021/038832 A1 | 3/2021 |
| WO | WO-2021/116395 A1 | 6/2021 |
| WO | WO 2021/116396 A1 * | 6/2021 |
| WO | WO-2021/163148 A1 | 8/2021 |
| WO | WO-2021/211548 A1 | 10/2021 |
| WO | WO-2022/103280 A1 | 5/2022 |
| WO | WO 2023/010170 A1 * | 2/2023 |

OTHER PUBLICATIONS

Machine-generated English translation of CN 205662436, generated on Jan. 2, 2024.*

Alemu AW et al., "Use of 3-nitrooxypropanol in a commercial feedlot to decrease enteric methane emissions from cattle fed a corn-based finishing diet" J Anim Sci. Jan. 1, 2021;99(1):skaa394. doi: 10.1093/jas/skaa394. (2021).

Anderson RC et al., "Ruminal Fermentation of Anti-Methanogenic Nitrate- and Nitro-Containing Forages In Vitro" Front Vet Sci. Aug. 11, 2016;3:62. doi: 10.3389/fvets.2016.00062. eCollection 2016. (2016).

Dijkstra J et al., "Short communication: Antimethanogenic effects of 3-nitrooxypropanol depend on supplementation dose, dietary fiber content, and cattle type" J Dairy Sci. Oct. 2018;101(10):9041-9047. doi: 10.3168/jds.2018-14456. Epub Jul. 25, 2018. (2018).

Duin et al., "Mode of action uncovered for the specific reduction of methane emissions from ruminants by the small molecule 3-nitrooxypropanol" Proc Natl Acad Sci U S A. May 31, 2016;113(22):E3185. doi: 10.1073/pnas.1607088113. Epub May 23, 2016. (2016).

Garcia F et al., "3-Nitrooxypropanol substantially decreased enteric methane emissions of dairy cows fed true protein- or urea-containing diets" Heliyon. Jun. 16, 2022;8(6):e09738. doi: 10.1016/j.heliyon.2022.e09738. eCollection Jun. 2022. (2022).

Gruninger RJ et al., "Application of 3-nitrooxypropanol and canola oil to mitigate enteric methane emissions of beef cattle results in distinctly different effects on the rumen microbial community" Anim Microbiome. May 31, 2022;4(1):35. doi: 10.1186/s42523-022-00179-8. (2022).

Guyader J et al., "Redirection of Metabolic Hydrogen by Inhibiting Methanogenesis in the Rumen Simulation Technique (RUSITEC)" Front Microbiol. Mar. 14, 2017;8:393. doi: 10.3389/fmicb.2017.00393. eCollection 2017. (2017).

Hristov AN et al., "An inhibitor persistently decreased enteric methane emission from dairy cows with no negative effect on milk production" Proc Natl Acad Sci U S A. Aug. 25, 2015;112(34):10663-8. doi: 10.1073/pnas.1504124112. Epub Jul. 30, 2015. (2015).

(56) References Cited

OTHER PUBLICATIONS

Hristov AN et al., "Short communication: Relationship of dry matter intake with enteric methane emission measured with the GreenFeed system in dairy cows receiving a diet without or with 3-nitrooxypropanol" Animal. Sep. 2020;14(S3):s484-s490. doi: 10.1017/S1751731120001731. Epub Jul. 28, 2020. (2020).

Liu Z et al., "Effects of combined addition of 3-nitrooxypropanol and vitamin B(12) on methane and propionate production in dairy cows by in vitro-simulated fermentation" J Dairy Sci. Jan. 2023;106(1):219-232. doi: 10.3168/jds.2022-22207. Epub Nov. 7, 2022. (2023).

Liu Z et al., "Synergistic Effects of 3-Nitrooxypropanol with Fumarate in the Regulation of Propionate Formation and Methanogenesis in Dairy Cows In Vitro" Appl Environ Microbiol. Mar. 22, 2022;88(6):e0190821. doi: 10.1128/AEM.01908-21. Epub Jan. 26, 2022. (2022).

Lopes JC et al., "Effect of 3-nitrooxypropanol on methane and hydrogen emissions, methane isotopic signature, and ruminal fermentation in dairy cows" J Dairy Sci. Jul. 2016;99(7):5335-5344. doi: 10.3168/jds.2015-10832. Epub Apr. 13, 2016. (2016).

Martinez-Fernandez G et al., "3-NOP vs. Halogenated Compound: Methane Production, Ruminal Fermentation and Microbial Community Response in Forage Fed Cattle" Front Microbiol. Aug. 7, 2018;9:1582. doi: 10.3389/fmicb.2018.01582. eCollection 2018. (2018).

Martínez-Fernández G et al., "Effects of ethyl-3-nitrooxy propionate and 3-nitrooxypropanol on ruminal fermentation, microbial abundance, and methane emissions in sheep" J Dairy Sci. 2014;97(6):3790-9. doi: 10.3168/jds.2013-7398. Epub Apr. 14, 2014. (2014).

Melgar A et al., "Dose-response effect of 3-nitrooxypropanol on enteric methane emissions in dairy cows" J Dairy Sci. Jul. 2020;103(7):6145-6156. doi: 10.3168/jds.2019-17840. Epub Apr. 8, 2020. (2020).

Nkemka VN et al., "Treatment of feces from beef cattle fed the enteric methane inhibitor 3-nitrooxypropanol" Water Sci Technol. Aug. 2019;80(3):437-447. doi: 10.2166/wst.2019.302. (2019).

Ochoa-García PA et al., "In vitro reduction of methane production by 3-nitro-1-propionic acid is dose-dependent" J Anim Sci. Mar. 1, 2019;97(3):1317-1324. doi: 10.1093/jas/skz012. (2019).

Pitta DW et al., "Temporal changes in total and metabolically active ruminal methanogens in dairy cows supplemented with 3-nitrooxypropanol" J Dairy Sci. Aug. 2021;104(8):8721-8735. doi: 10.3168/jds.2020-19862. Epub May 21, 2021. (2021).

Pitta DW et al., "The effect of 3-nitrooxypropanol, a potent methane inhibitor, on ruminal microbial gene expression profiles in dairy cows" Microbiome. Sep. 13, 2022;10(1):146. doi: 10.1186/s40168-022-01341-9. (2022).

Reynolds CK et al., "Effects of 3-nitrooxypropanol on methane emission, digestion, and energy and nitrogen balance of lactating dairy cows" J Dairy Sci. 2014;97(6):3777-89. doi: 10.3168/jds.2013-7397. Epub Apr. 3, 2014. (2014).

Romero-Pérez A et al., "Rapid Communication: Evaluation of methane inhibitor 3-nitrooxypropanol and monensin in a high-grain diet using the rumen simulation technique (Rusitec)" J Anim Sci. Sep. 2017;95(9):4072-4077. doi: 10.2527/jas2017.1896. (2017).

Schilde M et al., "Effects of 3-nitrooxypropanol and varying concentrate feed proportions in the ration on methane emission, rumen fermentation and performance of periparturient dairy cows" Arch Anim Nutr. Apr. 2021;75(2):79-104. doi: 10.1080/1745039X.2021.1877986. Epub Mar. 1, 2021. (2021).

van Gastelen S et al., "Methane mitigation potential of 3-nitrooxypropanol in lactating cows is influenced by basal diet composition" J Dairy Sci. May 2022;105(5):4064-4082. doi: 10.3168/jds.2021-20782. Epub Feb. 25, 2022. (2022).

van Lingen HJ et al., "Inhibited Methanogenesis in the Rumen of Cattle: Microbial Metabolism in Response to Supplemental 3-Nitrooxypropanol and Nitrate" Front Microbiol. Jul. 27, 2021;12:705613. doi: 10.3389/fmicb.2021.705613. eCollection 2021. (2021).

Vyas D et al., "Effects of sustained reduction of enteric methane emissions with dietary supplementation of 3-nitrooxypropanol on growth performance of growing and finishing beef cattle" J Anim Sci. May 2016;94(5):2024-34. doi: 10.2527/jas.2015-0268. (2016).

Vyas D et al., "The combined effects of supplementing monensin and 3-nitrooxypropanol on methane emissions, growth rate, and feed conversion efficiency in beef cattle fed high-forage and high-grain diets" J Anim Sci. Jun. 29, 2018;96(7):2923-2938. doi: 10.1093/jas/sky174. (2018).

Yanibada B et al., "Milk metabolome reveals variations on enteric methane emissions from dairy cows fed a specific inhibitor of the methanogenesis pathway" J Dairy Sci. Dec. 2021;104(12):12553-12566. doi: 10.3168/jds.2021-20477. Epub Sep. 14, 2021. (2021).

Zhang et al., "3-Nitrooxypropanol supplementation had little effect on fiber degradation and microbial colonization of forage particles when evaluated using the in SITU ruminal incubation technique" J Dairy Sci. Oct. 2020;103(10):8986-8997. doi: 10.3168/jds.2019-18077. Epub Aug. 26, 2020. (2020).

International Search Report and Written Opinion for Application No. PCT/US2023/026747 dated Sep. 29, 2023.

Lil'Drug Store Products, Inc., Bayer-aspirin tablet, Label, Updated Jul. 12, 2021, [retrieved Aug. 16, 2023].

\* cited by examiner

Figure 14

| Material | Supplier | PCL65 | PCL75 | STR45 | STR45-STMP | STR45-BPO | LGN50 | LGN50-STMP | LGN50-BPO | ECS5-10NOP | ECS26-5NOP |
|---|---|---|---|---|---|---|---|---|---|---|---|
| | | | | | Weight Percent (%) | | | | | | |
| Polycaprolactone | Ingenity CAPA 6800 | 65.0% | 75.0% | 45.0% | 45.0% | 45.0% | 50.0% | 50.0% | 50.0% | 50.0% | 52.6% |
| Activated charcoal | Norit SA2 | 20.0% | 15.0% | 20.0% | 20.0% | 20.0% | 20.0% | 20.0% | 20.0% | 25.0% | 26.3% |
| 2-NOP | Ingredion Melojel | 15.0% | 10.0% | 15.0% | 15.0% | 15.0% | 15.0% | 15.0% | 15.0% | 10.0% | 5.3% |
| Starch | Ingredion Melojel | | | 15.0% | 15.0% | 15.0% | | | | | |
| Insoluble Lignin | Anbeed TCI | | | 5.0% | 5.0% | 5.0% | 15.0% | 15.0% | 15.0% | | |
| Ethyl Cellulose | Sigma-Aldrich | | | | | | | | | 15.0% | 15.8% |
| Ox rxnl solids | | | | | | | | | | | |
| Glycerol monooleate | Aaron Chemicals | 0.5% | 0.5% | 0.5% | 0.5% | 0.5% | 0.5% | 0.5% | 0.5% | 0.5% | 0.5% |
| Trisodium Trimetaphosphate | Sigma-Aldrich | | | | 5.0% | | | 5.0% | | | |
| Benzoyl Peroxide | Fisher Scientific | | | | | 3.0% | | | 3.0% | | |

COMPOSITIONS AND METHODS FOR REDUCING DELETERIOUS ATMOSPHERIC GAS EMISSIONS FROM FLOODED ECOSYSTEMS

CROSS-REFERENCE TO RELATED APPLICATIONS

This application claims the benefit of priority to U.S. Provisional Application No. 63/357,952 filed on Jul. 1, 2022, the contents of which are hereby incorporated by reference in their entirety.

BACKGROUND OF THE INVENTION

Greenhouse gases absorb and scatter infrared radiation in the wavelength range emitted by Earth. The most abundant deleterious atmospheric gases in Earth's atmosphere include water vapor ($H_2O$), carbon dioxide ($CO_2$), methane ($CH_4$), nitrous oxide ($N_2O$), ozone ($O_3$), and chloro-, hydrofluoro-, and perfluorocarbons. Aside from purely human-produced synthetic halocarbons, most deleterious atmospheric gases have both natural and human-caused sources, and atmospheric concentrations of deleterious atmospheric gases fluctuate according to the relative rate of production and sequestration. Since the beginning of the Industrial Revolution, the concentrations of many of the deleterious atmospheric gases have increased directly or indirectly through human-related activities including oil and gas production and use, deforestation, waste, power plants, transport, consumerism, farming and agriculture, industrialization, and cement production from limestone. Increases in deleterious atmospheric gases are demonstrating long term changes to the Earth's climate, i.e. climate change, and as a result, temperatures are rising world-wide, droughts are becoming longer and more extreme, fires are burning more intensely both during the day and throughout the night, tropical storms are becoming more severe due to warmer ocean water temperatures, mountain range and polar area snow pack is lower and the snow melts faster, glaciers are melting at a faster rate, sea ice in the Arctic Ocean around the North Pole is melting faster, permafrost is melting releasing additional methane into the atmosphere, sea levels are rising threatening coastal communities and estuarine ecosystems, among others.

Accordingly, there is a need for compositions and methods that reduce the rate of production of and/or increase the rate of sequestration of deleterious atmospheric gases and/or precursors thereof.

SUMMARY

In some embodiments, the invention provides compositions and methods for reducing emissions of deleterious atmospheric gases and/or precursors thereof from a flooded ecosystem. In some embodiments, a composition for reducing emissions of deleterious atmospheric gases and/or precursors thereof from a flooded ecosystem or a method for use thereof comprises one or more small molecules that reduce the production of one or more deleterious atmospheric gases and/or precursors thereof and one or more agriculturally suitable carriers. The one or more agriculturally suitable carriers may be a solid carrier, such as attapulgite, kaolinite, fuller's earth, calcium carbonate, perlite, diatomaceous earth, calcium silicate, fly ash, a polysaccharide, a disaccharide, a monosaccharide, a gum, a natural or synthetic derivative thereof, or a combination thereof. In other embodiments, the one or more solid carriers comprise a saccharide comprising cellulose, xantham gum, karaya gum, ethylcellulose, inositol, galactose, arabinose, lactose, lactulose, mannitol, mannose, sorbose, turanose, platinose, or a combination thereof.

In some embodiments, the one or more solid carriers is inert. In some embodiments, the one or more solid carriers is water soluble.

In some embodiments, the composition comprises one or more additives with a density greater than water and/or one or more additives that reduces the rate of dissolution of the composition in water.

In some embodiments, the composition has a density of at least 1.1, preferably about 1.1 mg/mL to about 3 mg/mL, about 1.5 to about 3 mg/mL, about 1.5 to about 2.5 mg/mL, or about 1.5 to about 2 mg/mL.

In some embodiments, the one or more additives with a density greater than water comprise silica, attapulgite, kaolinite, fuller's earth, calcium carbonate, perlite, diatomaceous earth, calcium silicate, fly ash, or any combination thereof.

In some embodiments, the one or more additives that reduce the rate of dissolution of the composition reduces a rate of release of the one or more small molecules into the flooded ecosystem.

In some embodiments, the composition dissolves occurs over at least about 1, 2, 3, 4, 5, 6, 7, 14, 21, 28, 35, 42, 49, 56, 63, 70, 77, 84, 91, 98, 105, 112, 119, 126, 133, 140, and/or not more than about 2, 3, 4, 5, 6, 7, 14, 21, 28, 35, 42, 49, 56, 63, 70, 77, 84, 91, 98, 105, 112, 119, 126, 133, 140, or 147 days, preferably 7-63 days, more preferably about 7-42 days, even more preferably 14-42 days yet even more preferably 14-28 days.

In some embodiments, the composition comprises particles having a uniform size distribution, while in other embodiments, the composition comprises particles having a non-uniform size distribution.

In some embodiments, the particles comprise a spherical-, square-, rectangular-, capsular-, cylindrical-, conical-, ovular-, triangular-, diamond-, or disk-like shape.

In some embodiments, the composition comprises a plurality of populations of particles, wherein each population or particles comprises a different formulation, a different shape, and/or a different size distribution. For example, the plurality of populations of particles may comprise a first population and a second population. In some embodiments, the population of granular particles further comprises at least 1, 2, 3, 4, 5, 5, 6, 8, or 9 and/or no more than 4, 5, 6, 7, 8, 9, or 10 additional populations, for example 3-10 additional populations, preferably 3-7 additional populations, more preferably 3-5 additional populations.

In certain embodiments, the first population comprises an immediate release formulation, while the second population comprises a delayed release formulation, such that the second population dissolves and/or releases the one or more small molecules that reduce the production of one or more deleterious atmospheric gases and/or precursors after the first population.

In some embodiments, each additional population comprises a delayed release formulation, wherein each population dissolves and/or releases the one or more small molecules that reduce the production of one or more deleterious atmospheric gases and/or precursors at a different time than each of the other populations.

In some embodiments, the composition further comprises one or more agriculturally beneficial additives, such as a vitamin, a nutrient, an antibiotic, a fungicide, an herbicide, a fertilizer, or any combination thereof.

In some embodiments, the one or more small molecules comprise a molecule that interferes with the uptake and/or conversion of acetate, $H_2$, $CO_2$, methanol, monomethylamine, dimethylamine, trimethylamine, nitric oxide, or a combination thereof.

In some embodiments, the one or more small molecules reduces the production of one or more deleterious atmospheric gases and/or precursors interact an enzyme selected from the group consisting of 3-(methylthio)propanoate:coenzyme M methyltransferase, acetate kinase, acetyl-CoA decarbonylase, acetyl-CoA decarbonylase/synthase complex $\alpha_2\epsilon_2$, acetyl-CoA decarbonylase/synthase complex β, acetyl-CoA decarbonylase/synthase complex γδ, acetyl-CoA synthase, carbon monoxide dehydrogenase, carbonic anhydrase, Co-methyltransferase, coenzyme M reductase, cyclohydrolase, dehydrogenase, dimethylamine-[corrinoid protein] Co-methyltransferase, $F_{420}$-dependent methylene-$H_4$MPT reductase, $F_{420}$-dependent methylene-$H_4$SPT dehydrogenase, formylmethanofuran dehydrogenase, formylmethanofuran:$H_4$MPT formyltransferase, formylmethanofuran:$H_4$SPT formyltransferase, formyltransferase, $H_2$-forming methylene-$H_4$MPT dehydrogenase, methanol-5-hydroxybenzimidazolylcobamide Co-methyltransferase, methenyl-$H_4$MPT cyclohydrolase, methyl-coenzyme M reductase, methyl-$H_4$SPT:COM methyltransferase, methylated [methylamine-specific corrinoid protein]:coenzyme M methyltransferase, methylcobamide:COM methyltransferase, methylthiol:coenzyme M methyltransferase, methyltransferase, MtaC protein:coenzyme M methyltransferase, phosphotransacetylase, tetrahydromethanopterin S-methyltransferase, tetramethylammonium methyltransferase, trimethylamine-corrinoid protein Co-methyltransferase, and any combination thereof.

In some embodiments, the one or more small molecules that reduce the production of one or more deleterious atmospheric gases and/or precursors interact with methyl-coenzyme M reductase (MCR).

In some embodiments, the one or more small molecules that reduce the production of one or more deleterious atmospheric gases and/or precursors comprise a compound having the formula $R^1$—[$CH_2$]n-$ONO_2$
wherein
n is an integer from 1 to 15
$R^1$ is selected from the group consisting of H, $C_1$-$C_6$alkyl, phenyl, —OH, —$NH_2$, —CN, —COOH, —O(C=O)$R^3$, —NHC(=O)$R^3$, $SO_2NHR^3$, or —$ONO_2$, —SH and $R^3$ is $C_1$-$C_6$alkyl, phenyl, pyridyl;
with the proviso that when n is >3 the hydrocarbon chain may be interrupted by —O— or —NH—.

In some embodiments, the one or more small molecules that reduce the production of one or more deleterious atmospheric gases and/or precursors comprises 3-nitrooxypropanol, 9-nitrooxynonanol, 5-nitrooxy pentanoic acid, 6-nitrooxy hexanoic acid, bis(2-hydroxyethyl)amine dinitrate, 1,4-bis-nitrooxybutane, 1,5-bis-nitrooxypentane, or any combination thereof. Preferably, the one or more small molecules is 3-nitrooxypropanol (3-NOP).

In some embodiments, the one or more deleterious atmospheric gases and/or precursors thereof are microbially-derived.

In some embodiments, the one or more deleterious atmospheric gases comprise carbon dioxide, methane, nitrous oxide, or a combination thereof.

In some embodiments, the one or more deleterious atmospheric gas precursor comprises acetate, hydrogen, carbon dioxide, or a combination thereof.

In some embodiments, the microorganism comprises one or more methanogens, for example suitable methanogens comprise a species of *Methanopyrales, Methanococcales, Methanobacteriales, Methanosarcinales, Methanomicrobiales, Methanocellales, Methanomassiliicoccales, Halobacteriales, Thermoplasmatalaltes*, or any combination thereof.

In some embodiments, the microorganism comprises an archaea.

In some embodiments, wherein the flooded ecosystem comprises a wetland. In some embodiments, the flooded ecosystem comprises hydric soil. The wetland may be lagoon, wet meadow, marsh, swamp, peatland, mire, bog, fen, mangrove forest, carr, pocosin, floodplain, vernal pool, paddy field, or a suitable flooded agricultural field. In some embodiments, the wetland is tidal, while in other embodiments, the wetland is non-tidal.

In some embodiments, the flooded ecosystem comprises an anaerobic or hypoxic environment.

In some embodiments, the flooded ecosystem comprises fresh water, brackish water, or salt water.

The present invention also provides a method for reducing emissions of deleterious atmospheric gases and/or precursors thereof from a flooded ecosystem comprising applying any of the aforementioned compositions to the flooded ecosystem. In some embodiments, the method further comprises reapplying the composition after a period of time, such as from about 7 days to about 28 days.

In some embodiments, the composition is delivered aerially, such as by drone.

BRIEF DESCRIPTION OF THE DRAWINGS

FIG. 14 is a table showing the composition of various polycaprolactone-based formulations according to some embodiments of the invention.

DETAILED DESCRIPTION

I. Introduction

Figure 1:
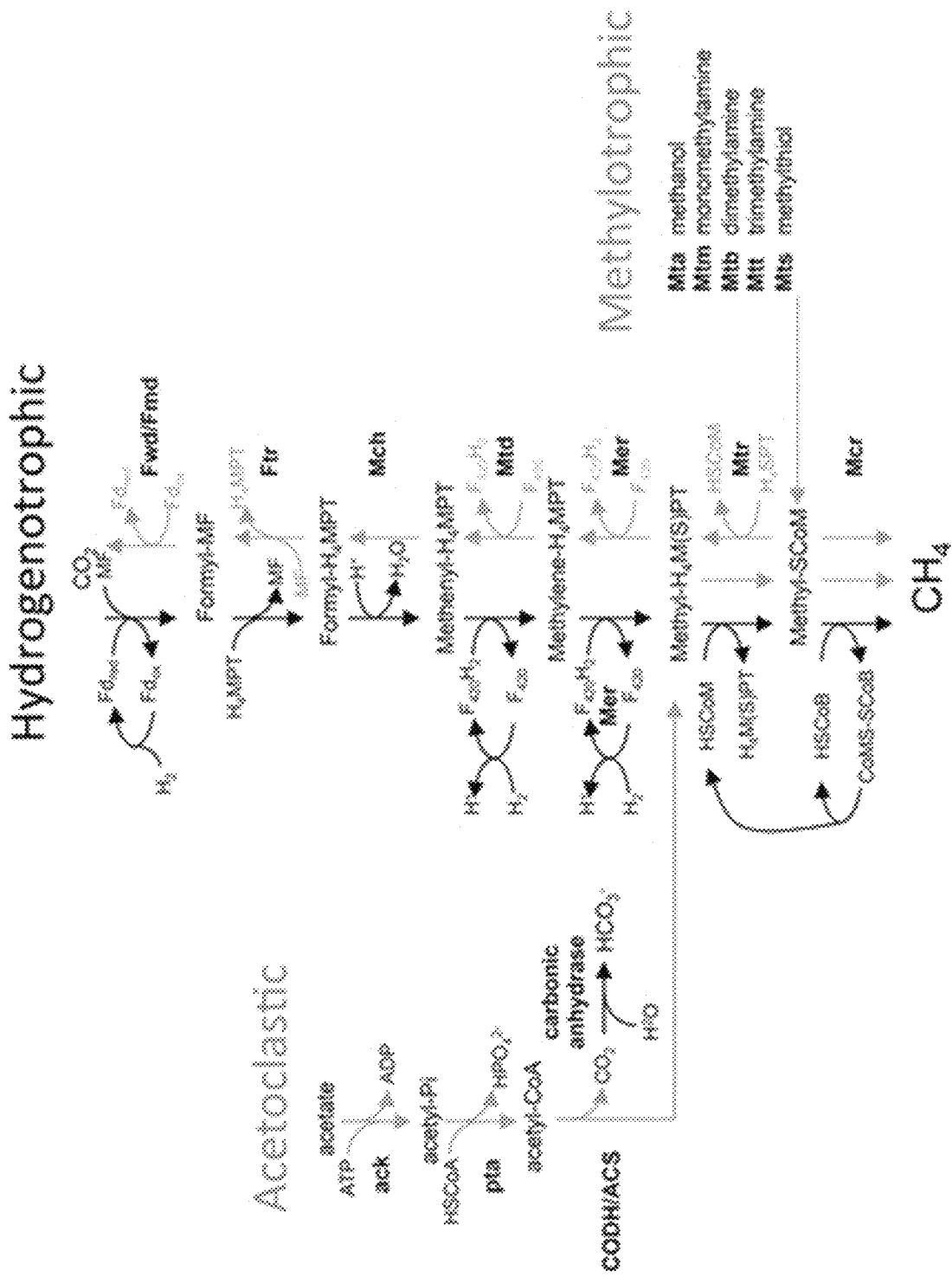
FIG. 1 is a schematic of a biochemical pathway and enzymes for the production of methane from acetate (i.e., the acetoclastic pathway), hydrogen and carbon dioxide (i.e., the hydrogenotrophic pathway), and methanol and derivatives thereof (i.e., the methylotrophic pathway).

Climate change is a global problem requiring innovative solutions to reduce production of and/or increase the sequestration of deleterious atmospheric gases and/or precursors thereof. The present invention relates to compositions, methods, and/or kits that reduce global deleterious atmospheric gases and/or precursors thereof. In preferred embodiments, provided herein are compositions, methods, and/or kits that reduce the production of deleterious atmospheric gases and/or precursors thereof. The deleterious atmospheric gases and/or precursors thereof to be reduced can be generated from any suitable production source, such as flooded ecosystems and/or agriculturally relevant ecosystems, for example, farming sites. In certain embodiments, provided herein are compositions, methods, and/or kits comprising one or more small molecules that affect the production of one or more deleterious atmospheric gases and/or precursors thereof. The one or more small molecules can be formulated in any suitable manner, for example, as a solid or liquid. In certain embodiments, the solid and/or liquid formulations are delivered to the site of use by human and/or by machine. In preferred embodiments, the one or more small molecules that affect the production of one or more deleterious atmospheric gases and/or precursors thereof target microorganisms.

II. Ecosystems

A. Flooded Ecosystems

In certain embodiments, provided herein are compositions, methods, and/or kits for use in flooded ecosystems. As used herein, the term "flooded ecosystem" includes an area where water is present at or near the surface of the soil for varying periods of time during the year. In certain cases, a flooded ecosystem comprises water at or near the surface of the soil for at least a portion of the growing season. The flooded ecosystem can be any suitable flood ecosystem, such as a wetland, for example a lagoon, wet meadow, marsh, swamp, peatland, mire, bog, fen, mangrove forest, carr, pocosin, floodplain, vernal pool, paddy field, an agricultural field, or a combination thereof. In certain embodiments, the wetland is tidal or non-tidal. In certain embodiments, the wetland comprises freshwater, brackish water, or salt water. In a preferred embodiment, the flooded ecosystem comprises a paddy field, more preferably a rice paddy.

Typically, the flooded ecosystem comprises hydric soil, i.e., soil formed under conditions of saturation, flooding or ponding for a period of time during the growing season. One of many characteristics of hydric soil includes the presence of hypoxic and/or anaerobic conditions in the soil, wherein an environment with little to no oxygen provides favorable conditions for anaerobic organisms. For example, the anaerobic environment generated from rice farming, e.g., a rice paddy, promotes the growth of methanogenic microorganisms whose activity results in the generation of one or more deleterious atmospheric gases and/or precursors thereof, including methane. It is estimated that methane from rice production contributes to 1.5% of the total global deleterious atmospheric gas emissions. Provided herein, are compositions, methods, and/or kits for reducing the production of one or more deleterious atmospheric gases and/or precursors thereof from flooded ecosystems.

B. Agriculturally Relevant Ecosystems

In certain embodiments, provided herein are compositions, methods, and/or kits for use in suitable agriculturally relevant ecosystems. In certain embodiments, the agriculturally relevant ecosystem comprises arable land and/or pastureland, such crop land, meadows, pastures, and/or forests. Provided herein, are compositions, methods, and/or kits for reducing the production of one or more deleterious atmospheric gases and/or precursors thereof from an agriculturally relevant ecosystem.

III. Microbial Sources of Deleterious Atmospheric Gases and/or Precursors Thereof A. Methanogens In certain embodiments, wherein the one or more deleterious atmospheric gases and/or precursors thereof are microbially derived, the microorganism can be any suitable microorganism, such as a methanogen, for example a *Methanopyrales, Methanococcales, Methanobacteriales, Methanosarcinales, Methanomicrobiales, Methanocellales, Methanomassiliicoccales, Halobacteriales, Thermoplasmataltes*, or a combination thereof. In certain embodiments, the methanogen comprises an archaea. In preferred embodiments, the microorganism comprises a methanogen.

B. Biochemical Pathways

In certain embodiments, the one or more deleterious atmospheric gases and/or precursors thereof are microbially derived through one or more biosynthetic pathway. The deleterious atmospheric gas can be any suitable deleterious atmosphere gas, such as carbon dioxide, methane, nitrous oxide, or a combination thereof. The deleterious atmospheric gas precursor can be any suitable precursor, such as acetate, hydrogen, carbon, methanol, monomethylamine, dimethylamine, trimethylamine, nitric oxide, or a combination thereof. In preferred embodiments, the deleterious atmosphere gas comprises carbon dioxide, hydrogen, or methane more preferably methane. In certain embodiments, wherein the resultant deleterious atmospheric gas comprises methane, the one or more biosynthetic pathways include the acetoclastic, hydrogenotrophic, and methylotrophic pathways, which differ based on the starting substrates, i.e., precursor, (FIG. 1), more preferably the acetoclastic or hydrogenotrophic pathways, even more preferably the acetoclastic pathway.

The acetoclastic pathway comprises a series of enzymes that convert the precursor acetate through a series of enzymatic conversions to methane. Starting from acetate, (1) acetate is converted to acetyl phosphate by acetate kinase (ack); (2) acetyl phosphate is converted to acetyl-CoA by phosphotransacetylase (pta); (3) the acetyl group from acetyla-CoA is transferred to a protein intermediate by acetyl-CoA decarbonylase; (4) the acetyl group is then transferred to tetrhydrosarcinapterin to form 5-methyl-tetrahydrosarcinapterin by methyltetrahydrosarcinapterin methyltransferase; (5) 5-methyl-tetrahydrosarcinapterin is converted to methyl-COM by methyl-$H_4$SPT:COM methyltransferase (Mtr); and (6) methyl-COM is reduced to methane by methyl-CoM reductase (Mcr) (FIGS. 1 and 2).

The hydrogenotrophic pathway comprises a series of enzymes that convert the precursors hydrogen and carbon dioxide to methane. Starting from carbon dioxide and hydrogen, (1) a formylmethanofuran dehydrogenase (Fwd/Fmd) produces a formylmethanofuran, (2) which is further converted into 5-formyl-tetrahydromethanopterin by a formylmethanofuran:$H_4$MPT formylatransfer (Ftr); (3) 5-formyl-tetrahydromethanopterin is further converted into 5,10-methenyltetrahydromethanopterin by methyl-$H_4$MPT cyclohydrolase (Mch); (4) 5,10-methenyltetrahydromethanopterin is converted to $N_6$-methyltetrahydromethanopterin by $F_{420}$-dependent methylene-$H_4$MPT reductase (Mer); (5) $N_6$-methyltetrahydromethanopterin is converted to methyl-CoM by methyl-$H_4$MPT:coenzyme M methyltransferase (Mtr); and (6) methyl-COM is reduced to methane by methyl-COM reductase (Mcr) (FIGS. 1 and 2).

Figure 2:
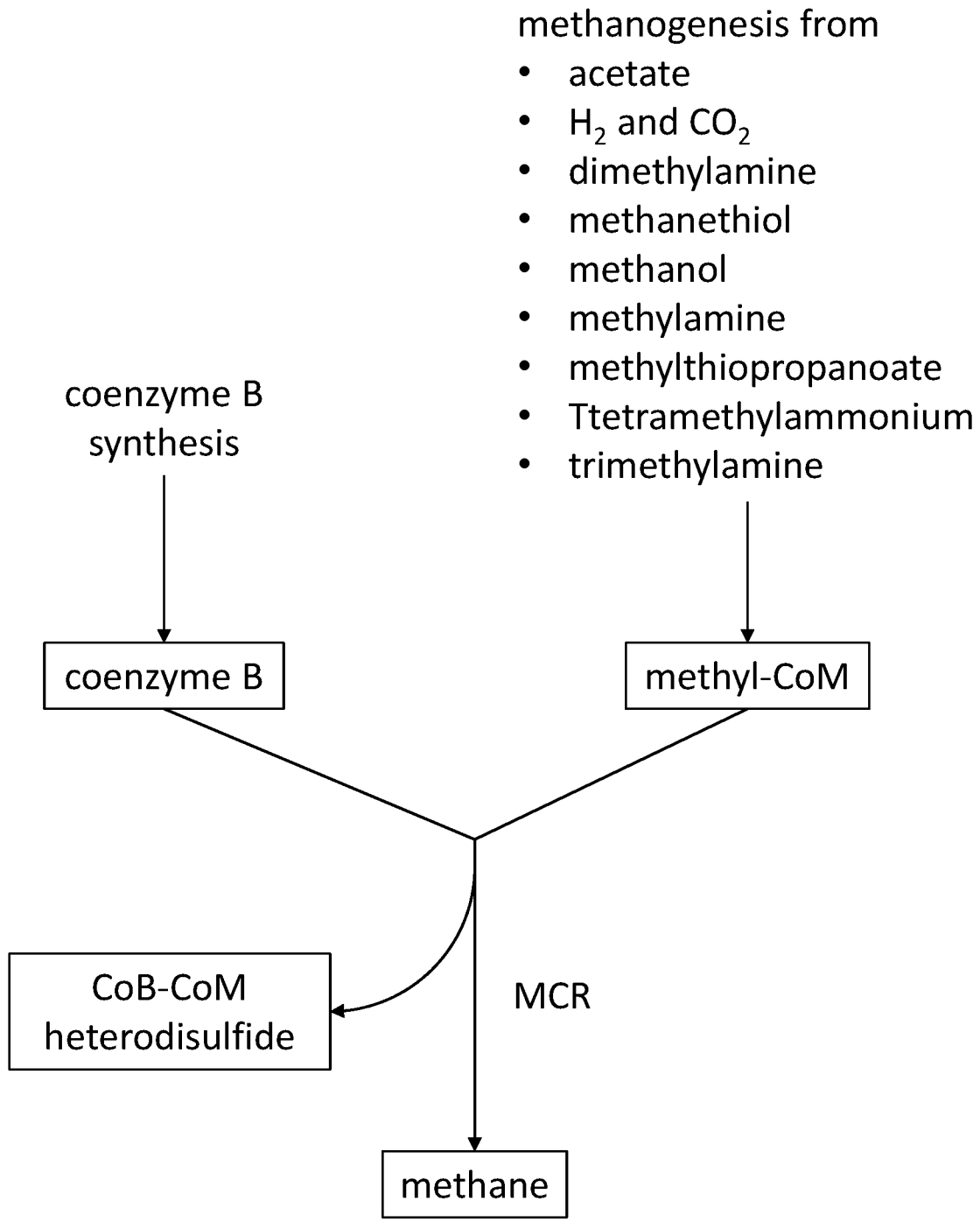
FIG. 2 is a schematic describing the reduction of methyl-COM and coenzyme B into methane by methyl-coenzyme M reductase (MCR), a key enzyme present in methane production via the acetoclastic, hydrogenotrophic, and methylotrophic pathways.

The methylotrophic pathway comprises a series of enzymes that convert one or more of dimethylamine, methanethiol, methanol, methylamine, methylthiopropanoate, tetramethylammonium, and/or trimethylamine into methyl-COM, wherein methyl-COM is reduced to methane by methyl-COM reductase (Mcr) (FIGS. 1 and 2).

Figure 3:
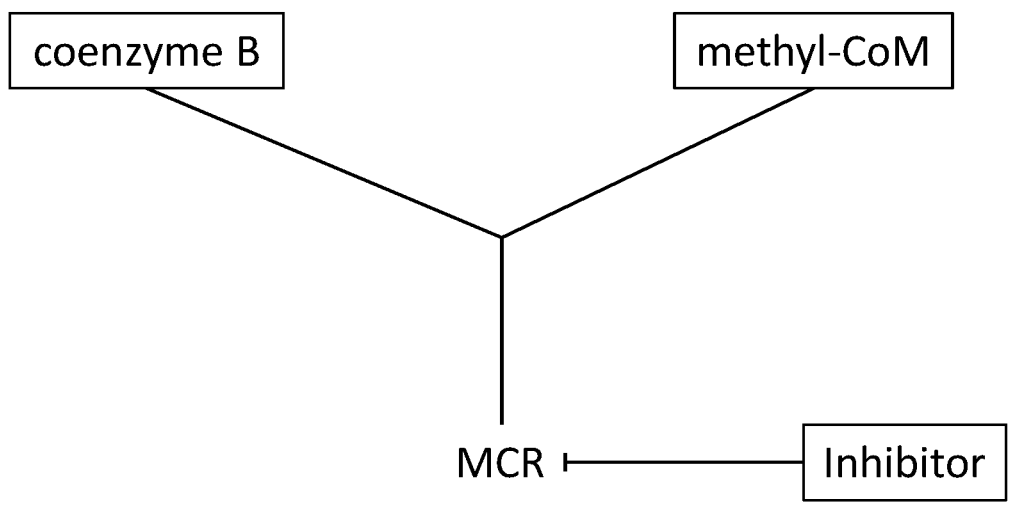
FIG. 3 is a schematic describing the application of small molecules that affect MCR activity to modulate methane production.

In certain embodiments, provided herein are compositions, methods, and/or kits comprising one or more small molecules that reduce the activity of one or more enzymes in one or more methane biosynthetic pathways. The enzyme can be any suitable enzyme, such as 3-(methylthio)propanoate:coenzyme M methyltransferase, acetate kinase, acetyl-CoA decarbonylase, acetyl-CoA decarbonylase/synthase complex $\alpha_2\varepsilon_2$, acetyl-CoA decarbonylase/synthase complex $\beta$, acetyl-CoA decarbonylase/synthase complex $\gamma\delta$, acetyl-CoA synthase, carbon monoxide dehydrogenase, carbonic anhydrase, Co-methyltransferase, coenzyme M reductase, cyclohydrolase, dehydrogenase, dimethylamine-[corrinoid protein] Co-methyltransferase, $F_{420}$-dependent methylene-$H_4$MPT reductase, $F_{420}$-dependent methylene-$H_4$SPT dehydrogenase, formylmethanofuran dehydrogenase, formylmethanofuran:HAMPT formyltransferase, formylmethanofuran:$H_4$SPT formyltransferase, formyltransferase, $H_2$-forming methylene-$H_4$MPT dehydrogenase, methanol-5-hydroxybenzimidazolylcobamide Co-methyltransferase, methenyl-$H_4$MPT cyclohydrolase, methyl-coenzyme M reductase, methyl-$H_4$SPT:COM methyltransferase, methylated [methylamine-specific corrinoid protein]:coenzyme M methyltransferase, methylcobamide:COM methyltransferase, methylthiol:coenzyme M methyltransferase, methyltransferase, MtaC protein:coenzyme M methyltransferase, phosphotransacetylase, tetrahydromethanopterin S-methyltransferase, tetramethylammonium methyltransferase, trimethylamine-corrinoid protein Co-methyltransferase, or a combination thereof. In a preferred embodiment, the enzyme comprises methyl-COM reductase (Mcr) (FIG. 3).

IV. Compositions for Reducing Production of Deleterious Atmospheric Gases and/or Precursors Thereof In certain embodiments provided herein are compositions. In certain embodiments, provided herein are compositions comprising one or more small molecules. In preferred embodiments, provided herein are compositions comprising one or more small molecules that reduce the production of one or more deleterious atmospheric gases and/or precursors thereof. The small molecule can be any suitable small molecule for reducing the production of one or more greenhouse gases and/or precursors thereof, for example a small molecule that interferes with the uptake and/or conversion of acetate, hydrogen, carbon dioxide, methanol, monomethylamine, dimethylamine, trimethylamine, nitric oxide, or a combination thereof, and/or a small molecule that interfere with the production of carbon dioxide, hydrogen nitrous oxide, or a combination thereof. In preferred embodiments, the small molecule interferes with the uptake and/or conversion of acetate, hydrogen and/or carbon dioxide and/or the production of carbon dioxide or methane, more preferably with the production of methane.

A. Small Molecules that Affect Production of Deleterious Atmospheric Gases and/or Precursors Thereof In certain embodiments, provided herein is a composition for reducing emissions of deleterious atmospheric gasses and/or precursors thereof from a flooded ecosystem comprising: one or more small molecules that reduce the production of one or more deleterious atmospheric gasses and/or precursors thereof. The one or more small molecules that reduce the production of one or more deleterious atmospheric gasses and/or precursors can be any suitable molecule.

In certain embodiments, the one or more small molecules that reduce the production of one or more deleterious atmospheric gasses and/or precursors comprises a compound with the formula the formula $R^1$—$[CH_2]n$-$ONO_2$ wherein n is an integer from 1 to 15;

$R^1$ is selected from the group consisting of H, $C_1$-$C_6$alkyl, phenyl, —OH, —$NH_2$, CN, —COOH, —O(C═O)$R^3$, —NHC(═O)$R^3$, $SO_2NHR^3$, or —$ONO_2$, —SH and $R^3$ is $C_1$-$C_6$alkyl, phenyl, pyridyl;

with the proviso that when n is >3 the hydrocarbon chain may be interrupted by —O— or —NH—.

In some embodiments, the one or more small molecules that reduce the production of one or more deleterious atmospheric gases and/or precursors comprises 3-nitrooxypropanol, 9-nitrooxynonanol, 5-nitrooxy pentanoic acid, 6-nitrooxy hexanoic acid, bis(2-hydroxyethyl)amine dinitrate, 1,4-bis-nitrooxybutane, 1,5-bis-nitrooxypentane, or any combination thereof. Preferably, the one or more small molecules is 3-nitrooxypropanol (3-NOP).

In some embodiments, the composition comprises about 1 to about 25% by weight of the small molecule, about 5 to about 20% by weight of the small molecule, or about 5 to about 15% by weight of the small molecule.

B. Solid Carriers

In certain embodiments, the composition further comprises one or more solid carriers. As used herein, the term "solid carrier" includes additives commonly used in the preparation of powderous formulations such as thickeners, for example gums or cellulose derivatives such as xanthan gum, karaya gum and/or ethylcellulose. The one or more solid carriers can be any agriculturally suitable carrier, such as attapulgite, kaolinite, fuller's earth, calcium carbonate, perlite, diatomaceous earth, calcium silicate, fly ash, a polysaccharide, a disaccharide, a monosaccharide, a gum, a natural or synthetic derivative thereof, or a combination thereof.

In certain embodiments, the one or more solid carriers comprises any carrier suitable for ingestion, such as a saccharide comprising cellulose, xantham gum, karaya gum, ethylcellulose, inositol, galactose, arabinose, lactose, lactulose, mannitol, mannose, sorbose, turanose, platinose, or a combination thereof.

In some embodiments, the carrier comprises attapulgite, kaolinite, fuller's earth, calcium carbonate, perlite, diatomaceous earth, calcium silicate, fly ash, a polysaccharide, a disaccharide, a monosaccharide, a gum, a natural or synthetic derivative thereof, or a combination thereof.

In other embodiments, the carrier comprises attapulgite, kaolinite, fuller's earth, calcium carbonate, perlite, diatomaceous earth, calcium silicate, fly ash, a polysaccharide, a disaccharide, a monosaccharide, a gum, silica, propylene glycol, hemp protein, biochar, montmorillonite, activated charcoal, lignin, wood flour, hemp protein, pea protein, soy protein, gelatin, casein, chitosan, talc, calcium phosphate, arginine, lysine, calcium carbonate, carbon black, glutamine, betaine, bismuth phosphate, bismuth citrate, iron phosphate, or any combination thereof.

In some embodiments, the carrier comprises the one or more solid carriers comprises a saccharide comprising cellulose, xanthan gum, karaya gum, ethylcellulose, inositol, galactose, arabinose, lactose, lactulose, mannitol, mannose, sorbose, turanose, platinose, or a combination thereof.

In some embodiments, the one or more solid carriers comprises a saccharide comprising cellulose, xanthan gum, karaya gum, ethylcellulose, inositol, galactose, arabinose, lactose, lactulose, mannitol, mannose, sorbose, turanose, platinose, carrageenan, cellulose acetate, hydroxypropyl cellulose, cellulose acteate phthalate, maltrodextran, dextran, inulin, corn starch, amylopectin, sodium startch glycolate, pentaerthritol, cyclodextrin, or a combination thereof.

In certain preferred embodiments, the the solid carrier comprises silica and ethylcellulose, more particularly about 10% to about 50% by weight of the silica and about 50 to about 90% by weight of the ethylceluose.

In other preferred embodiments, the solid carrier comprises silica and activated charcoal, particularly about 10% to about 90% by weight of the silica and about 10% to about 90% by weight of the activated charcoal.

In certain embodiments, the binder further comprises arginine, lysine, or both arginine and lysine. While not being bound by theory, it is believed that arginine and lysine are capable of forming hydrogen bonds with the small molecule, such as 3-NOP, thereby altering the release rate into the flooded ecosystem.

In other preferred embodiments, the carrier comprises activated charcoal and ethylcellulose, particularly about 10% to about 50% by weight of the activated charcoal and about 40 to about 90% by weight of the ethylcellulose.

In some embodiments, the carrier further comprises about 1 to about 10% by weight of sodium lignosulfate. While not being bound by theory, it is believed that sodium lignosulfate improves coating adhesion to the tablet resulting in a reduction in release rate of the small molecule.

In other embodiments, the carrier comprises arginine and polycaprolactone, such as about 10 to about 60% by weight of the arginine and about 30 to about 90% by weight of the polycaprolactone.

In other preferred embodiments, the carrier comprises 25% silica, 66% polycaprolactone, such as about 10 to about 60% by weight of the silica and about 30 to about 90% by weight of the polycaprolactone.

In certain embodiments, the composition comprises a granular shape. The composition may comprise any suitable shape, such as a spherical-, square-, rectangular-, capsular-, cylindrical-, conical-, ovular-, triangular-, diamond-, disk-like shape, or a combination thereof. In certain embodiments, the shape of the particle affects the rate of dissolution of the particle.

The granular particle can comprise any suitable texture, for example hard or soft. In certain embodiments, the texture of the particle affects the rate of dissolution of the particle. In certain embodiments, the composition comprises a combination of differently textured pellets each of which release the small molecule at different rates.

In certain embodiments, the granular particles comprise a uniform size distribution, for example about ±20%, ±15%, ±10%, ±5%, ±2%, or ±1% size distribution in the median particle size. In certain embodiments, the granular particles comprise a non-uniform size distribution, for example greater than about ±20%. In certain embodiments, the granular particles comprise a plurality of differently sized populations of granular particles each of which comprise a uniform size distribution.

In certain embodiments, the one or more solid carrier dissolves and thereby releases the one or more small molecules that reduce the production of greenhouse gases and/or precursors thereof. In a preferred embodiment, the one or more solid carriers will dissolve in water.

C. Extended and Delayed Release

It may be necessary to vary the rate of dissolution of the composition. For example, one may want to produce an extended-release formulation, wherein the composition releases the one or more small molecules over a period of time to maintain a suitable environmental concentration of the one or more small molecules. This can be beneficial to reduce the frequency of applications, for example to reduce labor costs and/or applications in rural and/or hard to reach environments. In certain embodiments, complete dissolution of the composition and full release of the one or more small molecules occurs over at least about 1, 2, 3, 4, 5, 6, 7, 14, 21, 28, 35, 42, 49, 56, 63, 70, 77, 84, 91, 98, 105, 112, 119, 126, 133, 140, and/or nor more than about 2, 3, 4, 5, 6, 7, 14, 21, 28, 35, 42, 49, 56, 63, 70, 77, 84, 91, 98, 105, 112, 119, 126, 133, 140, or 147 days, for example about 1 to about 147 days, preferably about 7 to about 63 days, more preferably about 7 to about 42 days even more preferably about 14 to about 42 days yet even more preferably about 14 to about 28 days.

In certain embodiments, the extended-release formula may comprise any suitable extended-release formula. In certain embodiments, the extended-release formula comprises one or more additives that reduce the rate of dissolution of the composition, one or more additives that reduce the rate of dissolution of the small molecule from the composition, one or more additives that comprise a membrane that dissolves over time, wherein the rate of dissolution of the membrane controls the rate of release of the one or more small molecules, a suitable alternative, or a combination thereof.

In certain embodiments, the population of granular particles comprises a plurality of populations of granular particles wherein each population comprises a different formulation and/or shape. In certain embodiments, the population of granular particles comprises a first population and a second population. In certain embodiments, the population of granular particles further comprises at least 1, 2, 3, 4, 5, 5, 6, 8, or 9 and/or no more than 4, 5, 6, 7, 8, 9, or 10 additional populations, for example a total of 3-10 additional populations, preferably 3-7 additional populations, more preferable 3-5 additional populations. In a preferred embodiment, each of the additional populations comprises a different formulation than the others.

In certain embodiments, the rate of dissolution of the granular particles is modulated by the size of the granular particle. In certain embodiments, smaller granular particles dissolve faster than larger granular particles, such that each successive larger population in the plurality of populations of differently size particles provides a delayed release compared to the smaller populations of particles. In certain embodiments, an increased proportion of larger to smaller granular particles in a population of granular particles results in slower rates of dissolution of the population of granular particles.

In certain embodiments, the first population of particles comprises an immediate release formulation. In certain embodiments, the second population comprises a delayed release formulation, wherein the second population dissolves and/or releases the one or more small molecules that reduce the production of one or more deleterious atmospheric gasses and/or precursors after the first population. In certain embodiments, each additional population comprises a delayed release formulation, wherein each population dissolves and/or releases the one or more small molecules that reduce the production of one or more deleterious atmospheric gasses and/or precursors at a different time than each of the other populations.

In some embodiments, an immediate release formulation releases the one or more small molecules that reduce the production of one or more deleterious atmospheric gases with about 1 day, 2 days, 3 days, 4 days, 5 days, or 6 days. In some embodiments, a delayed release formulation releases the one or small molecules after about 1 week or more, for example up to about 21 weeks.

In some embodiments, the first population of particles provides has a half-life for the one or more small molecules (such as about about 1 to 12 hours), the second population has a longer half-life (such as about 24 or more hours), each additional population has a longer half-life than the previous population such that an effective amount of the one or more small molecules is maintained for weeks or months. Thus, the present compositions advantageously do not, in such embodiments, require repeated, frequent applications to the flooded ecosystem.

In certain embodiments, the extended release happens within the first 10% of the half-life and then the 1st delayed happens with 1-2 half lives, then the next with 1-2 of the delayed release.

In some embodiments, the particles have a size ranging from about 1 mm to about 20 mm, about 1 to about 15 mm, about 1 to about 10 mm, about 5 to about 20 mm, about 5 to about 15 mm, or about 5 to about 10 mm.

Coatings

In certain embodiments, the composition may comprise a coating, for examples particles or tablet having a coating. The coating can comprise any suitable coating, such as a wax, a fat, or a synthetic polymer. In certain embodiments, the wax comprises organic compounds consisting of long alkyl chains, natural waxes (plant, animal) which are typically esters of fatty acids and long chain alcohols as well as synthetic waxes, which are long-chain hydrocarbons lacking functional groups. In certain embodiments, the fat comprises a wide group of compounds which are soluble in organic solvents and largely insoluble in water such as hydrogenated fats (or saturated fats) which are generally triesters of glycerol and fatty acids. Suitable fats can have natural or synthetic origin. In certain embodiment, the fat comprises glycerine monostearate, carnauba wax, candelilla wax, sugarcane wax, palmitic acid, stearic acid hydrogenated cottonseed oil, hydrogenated palm oil and hydrogenated rapeseed oil, or combinations thereof. Any suitable synthetic polymer can be used, such as poly-L-glutamic acid (PGA) and polylactic acid (PLA). In preferred embodiments, the synthetic polymer is at least partially water soluble.

The coating may be single layer or multiple layers, preferably two layers.

In some embodiments, the coating is selected from cellulose acetate phlalate, ethyl cellulose, hydroxypropyl cellulose, polycaprolactone, alginate, chitosan, polyethylene glycol, cellulose actate, triacetin, propylene glycol, n-methyl-2-pyrollidone, and any combination thereof.

In certain preferred embodiments, the coating comprises two or more polyelectrolytes, such as polystyrene sulfonate, polyethyleneimine, sodium lignosulfate, polyglutamic acid and poly-L-lysine, poly-L-arginine, polyallylamine hydrochloride, polyacrylic acid, or any combination thereof.

In some preferred embodiments, the polyelectrolytes comprise polyallylamine hydrochloride and sodium lignosulfate.

In some preferred embodiments, the polyelectrolytes comprise comprise polyallylamine hydrochloride and polystyrene suylfonate.

In other preferred embodiments, the polyelectrolytes comprise sodium lignosulfate and one of polyglutamic acid and poly-L-lysine, or poly-L-arginine, and sodium lignosulfate.

In still other preferred embodiments, the polyelectrolytes comprise polystyrene sulfonate and one of polyglutamic acid and poly-L-lysine, or poly-L-arginine.

The polyelectrolytes may, in certain embodiments, be chemically cross-linked with a cross-linking agent.

In certain embodiments, the composition comprises one or more coatings applied with minimal to no bubbles. Additionally or alternatively, the composition comprises one or more coatings that comprise a foam or a plurality of air bubbles. In certain cases, the foamed coating can temporarily alter the buoyancy of the composition. One such example includes a composition comprising a foamed coating that floats when initially applied to a flooded ecosystem, then, after a period of time, the air pockets in the foamed coating fill with water resulting in the composition sinking to the bottom of the flooded ecosystem. This may be advantageous when the composition must be distributed from a centralized water source to a plurality of downstream flood ecosystems. Additionally or alternative, this may be advantageous to allow a composition applied to a small portion of a large flooded ecosystem to more evenly distribute across the entirety of the surface before sinking to the floor of the flood ecosystem.

D. Additives With a Density Greater Than Water

In certain embodiments, the composition further comprises one or more additives with a density greater than water. For example, the additive may have a density greater than 1.1, preferably about 1.1 mg/mL to about 3 mg/mL, about 1.5 to about 3 mg/mL, about 1.5 to about 2.5 mg/mL, or about 1.5 to about 2 mg/mL. Suitable additives include silica, attapulgite, kaolinite, fuller's earth, calcium carbonate, perlite, diatomaceous earth, calcium silicate, fly ash, or a combination thereof. In certain embodiments, the one or more additives with a density greater than water result in the composition sinking below the water surface when applied to the flooded ecosystem. In certain embodiments, the one or more additives with a density greater than water result in the composition partially or completely sinking to the bottom of the flooded ecosystem. In preferred embodiments, the composition completely sinks to the bottom of the flooded ecosystem. In certain embodiments, the composition comprising the additive with a density greater than water has a density of at least 1.1, preferably about 1.1 mg/mL to about 3 mg/mL, about 1.5 to about 3 mg/mL, about 1.5 to about 2.5 mg/mL, or about 1.5 to about 2 mg/mL.

E. Agriculturally Beneficial Additives

In certain embodiments, the composition further comprises one or more agriculturally beneficial additives. The agriculturally beneficial additive can be any suitable additive depending on the application, such a vitamin, a nutrient, an antibiotic, a fungicide, an herbicide, a fertilizer, or a combination thereof.

In certain embodiments, the additive includes one or more suitable components that reduce methanogenesis by methanogens, such as, seaweed (e.g., *Asparagopsis taxiformis*), kelp, 3-nitrooxypropanol, anthraquinones, ionophores (e.g., monensin and/or lasalocid), polyphenols (e.g., saponins, tannins), organosulfurs (e.g., garlic extract), flavonoids (e.g., quercetin, rutin, kaempferol, naringin, and anthocyanidins; bioflavonoids from green citrus fruits, rose hips and black currants), carboxylic acid, terpenes (e.g., D-limonene, pinene and citrus extracts), or a combination thereof.

V. Methods for Reducing Production of Deleterious Atmospheric Gases and/or Precursors Thereof In certain embodiments provided herein are methods. In certain embodiments, provided herein are methods for using one or more small molecules that reduce the production of one or more deleterious atmospheric gases and/or precursors thereof. In certain embodiments, provided herein are methods for applying one or more small molecules that reduce the production of one or more deleterious atmospheric gases and/or precursors thereof to any suitable environment. The suitable environment can comprise any suitable environment as described in the Ecosystems section above. In preferred embodiments, the suitable environment comprises a flooded ecosystem, such as a rice paddy.

In certain embodiments, the method for reducing emissions of deleterious atmospheric gasses and/or precursors thereof from a flooded ecosystem comprises applying a composition comprising one or more small molecules that reduce the production of the deleterious atmospheric gasses and/or precursors thereof to the flooded ecosystem. The composition can comprise any suitable composition. In a preferred embodiment, the composition comprises any one of the compositions as described in the Compositions for reducing production of deleterious atmospheric gases and/or precursors thereof section above. In a more preferred embodiments, the composition comprises 3-NOP.

Figure 4:
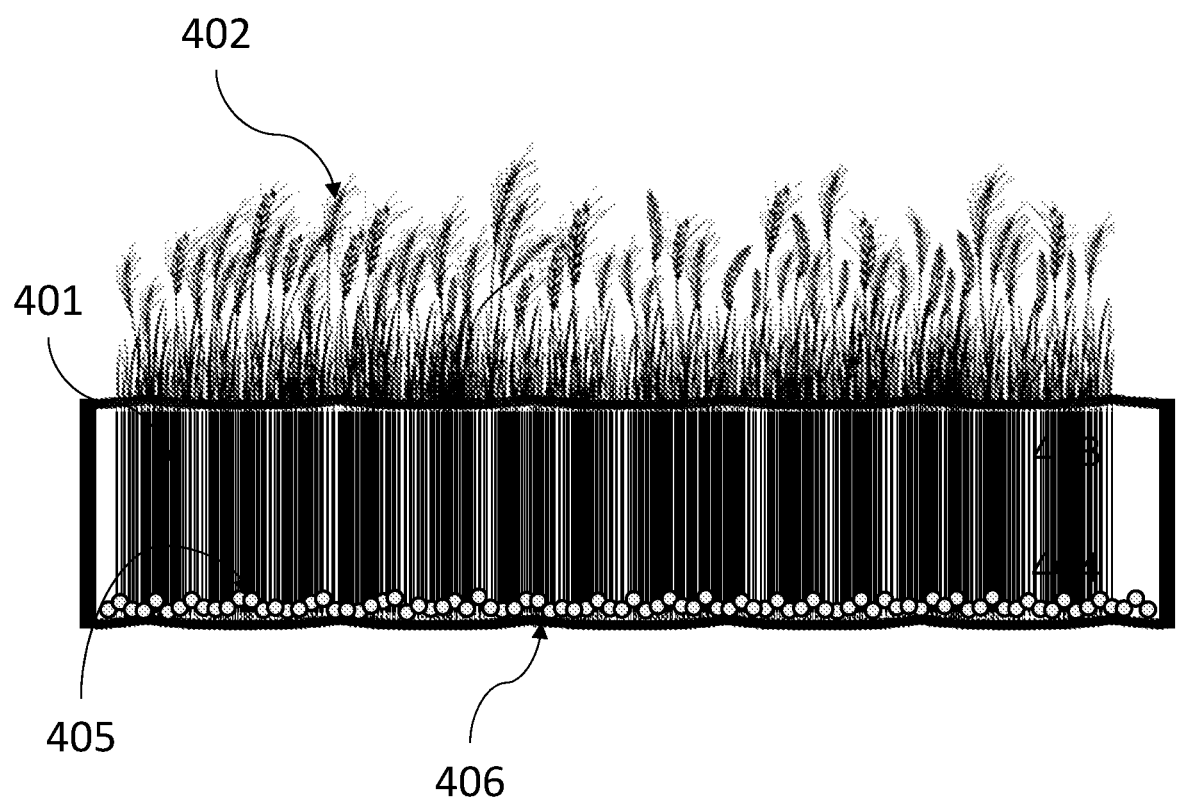
FIG. 4 is a cross-sectional diagram of the application of a composition for reduction of deleterious atmospheric gases and/or precursors thereof to a flooded ecosystem.

An exemplary method is shown in FIG. 4. In FIG. 4, the flood environment comprises a rice paddy (401) comprising one or more rice plants (402), wherein there is an oxygen-rich, anaerobic zone near the surface of the water (403) and an oxygen-deprived, anaerobic zone below the surface of the water (404). To the rice paddy, one or more compositions comprising one or more small molecules that reduce the production of one or more deleterious gases and/or precursors thereof (405) is applied, wherein the composition sinks to the paddy floor (406), wherein the dissolution of the composition reduces the production of the one or more deleterious gases and/or precursors thereof by one or more microorganisms.

In certain cases, the composition needs to be reapplied periodically to maintain a suitable concentration of the one or more small molecules. In certain embodiments, the method further comprises reapplying after a period of time a composition comprising one or more small molecules that reduce the production of the deleterious atmospheric gasses and/or precursors thereof to the flooded ecosystem. In certain embodiments, the method further comprises, reapplying again after a period of time a composition comprising one or more small molecules that reduce the production of the deleterious atmospheric gasses and/or precursors thereof to the flooded ecosystem. Any suitable number of reapplications may be performed as needed to maintain a an effective amount of the one or more small molecules. In some embodiments, the composition is reapplied after about 7 to about 28 days, about 7 to 46 days, about 7 to 92 days or about 7 to 147 days.

In certain embodiments, the composition is delivered to the one or more flooded ecosystems. Any suitable delivery method can be used, such as delivery with or without human intervention, for example aerial delivery, e.g., by drone.

Figure 5:
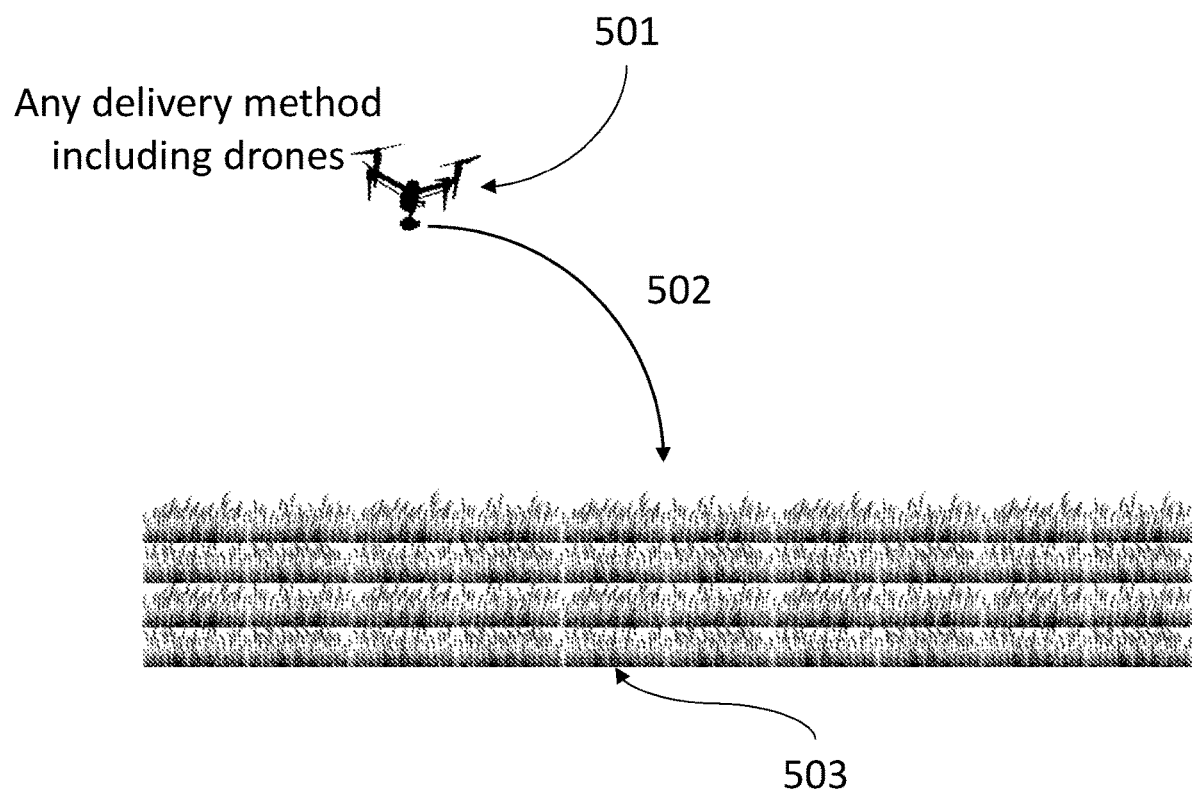
FIG. 5 shows aerial delivery of a composition for reduction of deleterious atmospheric gases and/or precursors thereof to a flooded ecosystem.

An exemplary method of delivery is shown in FIG. 5. In FIG. 5, one or more compositions comprising one or more small molecules that reduce the production of one or more deleterious gases and/or precursors thereof is loaded into an aerial vehicle, e.g., a drone, (501), wherein the aerial vehicle distributes (502) the composition to the flooded ecosystem (503).

Figure 6:
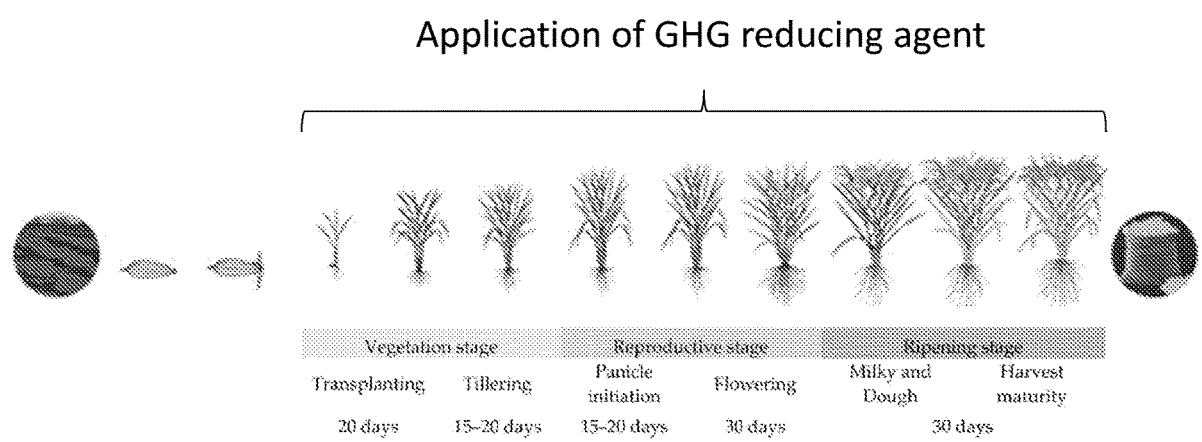
FIG. 6 shows an illustrative example of the application of a composition for reduction of deleterious atmospheric gases and/or precursors thereof throughout the rice lifecycle.

The composition can be applied at any suitable gestational period for the agricultural crop. For example, the composition can be applied during Vegetation, Reproductive, and/or Ripening stage during rice production in a paddy field as shown in FIG. 6.

In certain embodiments, the composition is delivered to one or more water sources, whereby the composition is delivered to the one or more flooded ecosystems upon use of the water from the source. For example, the water source can be a pool used to irrigate a cropland, e.g., a paddy field, wherein the composition is distributed to the cropland as the water is pulled from the water source.

In certain cases, the concentration of the one or more small molecules can be measured to ensure the presence of a suitable concentration of the one or more small molecules. Any suitable method may be used to measure the concentration, such as a strip test, liquid chromatography, or thin layer chromatography. The method can be performed with or without human intervention.

In some embodiments, the amount of the small molecule (e.g., 3-NOP) applied is from about 0.1 ppm to about 100 ppm per acre of flooded ecosystem. In other embodiments, the amount is about 0.5 ppm to about 50 ppm per acre. In still other embodiments, the amount is about 0.5, 1, 5, 10, 15, 20, 25, 30, 40, 45 or 50 pp per acre.

In some emobdiments, the amount of the small molecule applied is from about 0.5 ppm to about 50 ppm per acre VI. Kits for Reducing Production of Deleterious Atmospheric Gases and/or Precursors Thereof In certain embodiments, provided herein are kits. In certain embodiments, the kit comprises any one of the compositions as described in the Compositions for reducing production of deleterious atmospheric gases and/or precursors thereof section. In certain embodiments, the kit further comprises a suitable container for shipping.

VII. EXAMPLES

Synthesis of 3-NOP

Adapted from from "Structure-Based Design, Synthesis, and Biological Evaluation of Indomethacin Derivatives as Cyclooxygenase-2 Inhibiting Nitric Oxide Donors" (J. Med. Chem. 2007, 50, 6367-6382).

All reagents purchased from Sigma-Aldrich and Fisher Scientific and used as received.

3-Bromopropanol (78.0 g, 0.56 mol) in acetonitrile (300 mL) was added dropwise within minutes to a solution of silver nitrate (145.9 g, 0.86 mol) in acetonitrile (600 mL) and stirred at room temperature for 24 hr. The solution was protected from light by being covered with aluminum foil. After 24 hr, 5:1 excess of brine was added to the reaction mixture and stirred for 1 hr. Silver halide was filtered through Celite and filtrate was extracted with diethyl ether (300 mL×3). The organic layer was washed with brine (300 mL×3). Dried over sodium sulfate, and concentrated (59 g, 86% yield). Product confirmed via NMR (>97% purity based on HPLC).

3-NOP pH and Temperature Stability: Confirmed via HPLC over a 1-month time period at temperature between 4-30 C and pH 4-10.

3-NOP Volatility: 500 mg of 3-NOP in a 5 dram vial was left open to air at ~18-24 C at 15-30% RH over the course of 6 days. Average mass loss is ~0.25% per day.

Compaction Study

The viability of different binders for densification were examined. 0.5 g of powder was tableted under 20 kN in a 13 mm pellet die. Potential binders are summarized in Table 1.

TABLE 1

Potential binders ranked based on densification.

| 5: Unbreakable tablet by hand | 4: clean braking, no dust | 3: powdery break, retains moderate strength | 2: compacts, no strength 1: compacts, disintegrates 0: no compaction |
|---|---|---|---|
| Xanthan gum | Lignin | Pea protein | Chitosan |
| k-carrageenan | Inulin | Soy protein | Hydroxyethyl cellulose |
| Sodium alginate | Wood flour | Gelatin | Talc |
| Cellulose acetate | Corn Starch | Casein | Sodium starch glycolate |
| Ethyl cellulose | Amylopectin | | Pentaerythritol |
| Hydroxypropyl cellulose | Hemp protein | | Calcium phosphate |
| Cellulose acetate phthalate | | | Diatomaceous earth (Celite) |
| Maltodextrin | | | Biochar |
| Dextran | | | |

Tablets for Encapsulation of 3-NOP

A multilayer encapsulation system was employed for extended-release formulations consisting of 3 main parts:
1) Adsorbent—inert, non-toxic, solid-support for 3-NOP (ie. silica, biochar, activated charcoal, talc, arginine, lysine, calcium carbonate, carbon black, cyclodextrin, calcium phosphate, celite (diatomaceous earth), glutamine, betaine, bismuth phosphate, bismuth citrate, iron phosphate, etc)
2) Binder/matrix—allow for granulation of adsorbent to form solid core (ie, starches, flours, sugars, proteins, gums, gelatin, cellulose and derivatives, etc)
3) Coating—single to multilayer coatings to decrease water penetration and modify release kinetics All materials purchased from Sigma-Aldrich and Fisher Scientific and used as received unless otherwise specified.

Tablet Preparation

3-NOP was adsorbed onto the corresponding adsorbent at a given weight percent (noted in formulations) by dropwise addition to adsorbent stirring on a hot plate. The mixture was left to stir for more than 30 minutes until a free-flowing powder was obtained. The resulting mixture was speed mixed with the corresponding binder for 1 minute followed by compaction of in a carver press using an 8-13 mm pellet die under various forces of 10-60 kN.

Coated Tablet Preparation

Selected coating materials were dissolved in various solvents at 5-20 wt %. Tablets were then dip coated multiple times allowing for drying in between to give the desired coating weight.

3-NOP Release Quantification and Corresponding Tablet Formulations 13 mm, 0.5 g tablets were placed in a sealed 5 dram vial with 10 mL of distilled water and incubated at 70 F until full dissolution of 3-NOP. 1 mL aliquots were taken every few days and refreshed with 1 mL of distilled water. Aliquots were filtered through a 0.22 um PVDF filter before being quantified via HPLC.

Uncoated Tablets

All formulation percentages are based on weight. 2 replicates of 13 mm disc-shaped, 0.5 g tablets were compacted under 20 kN. The uncoated formulations had the following compositions:

AH-01—7.5% 3-NOP, 12.5% propylene glycol, 60% Cargill hemp protein

AH-02—8.57% 3-NOP, 22.86% Celite, 68.57% hemp protein

AH-03—8.57% 3-NOP, 22.86% Wakefield Biochar, 68.57% Cargill hemp protein

AH-04—8.57% 3-NOP, 22.86% K10 montmorillonite, 68.57% Cargill hemp protein

AH-05—8.57% 3-NOP, 22.86% activated charcoal, 68.57% Cargill hemp protein

The 3-NOP release of the uncoated tablets after 12 hours is shown in Table 2.

| Formula | Total Average Concentration of 3-NOP (mM) | Standard deviation (mM) |
|---|---|---|
| AH-01 | 24.56 | 2.09 |
| AH-02 | 24.50 | 1.76 |
| AH-03 | 19.61 | 0.17 |
| AH-04 | 33.10 | 0.10 |
| AH-05 | 18.58 | 0.07 |

Coated Tablets

Tablets for coating experiments consist of 10% 3-NOP, 20% Wakefield biochar, and 70% cellulose acetate (Mn: 50,000). Tablets were then coated with ~0.2 wt % of the corresponding coating material, as shown in the table in Table 3. The release profile over periods of 4, 6 and 11 days for each formula is also shown.

TABLE 3

3-NOP release profile of coated tablets over 4 days.

| | Time (days) | Total Average Concentration (mM) | Standard deviation (mM) |
|---|---|---|---|
| Cellulose Acetate Phthalate (CAP) | 4 | 34.21 | 2.23 |
| CAP | 6 | 30.65 | 0.04 |
| CAP | 11 | 32.38 | 0.24 |
| Ethyl cellulose (EC) | 4 | 29.92 | 0.06 |
| EC | 6 | 31.07 | 0.01 |
| EC | 11 | 31.50 | 0.26 |
| Hydroxy propyl cellulose (HPC) | 4 | 31.70 | 0.05 |
| HPC | 6 | 30.35 | 0.01 |
| HPC | 11 | 32.53 | 0.4 |
| Polycaprolactone (CAPA 6800) | 4 | 32.08 | 0.29 |
| CAPA 6800 | 6 | 31.00 | 0.14 |
| CAPA 6800 | 11 | 31.99 | 0.23 |
| Alignate (layer 1) Chitosan (layer 2) | 4 | 30.30 | 0.17 |
| Alignate (layer 1) Chitosan (layer 2) | 6 | 30.22 | 0.17 |
| Alignate (layer 1) Chitosan (layer 2) | 11 | 31.90 | 0.10 |
| Polycaprolactone Mn: 2000 | 4 | 33.68 | 0.01 |
| Polycaprolactone Mn: 2000 | 6 | 32.25 | 0.18 |
| Polycaprolactone Mn: 2000 | 11 | 33.23 | 0.09 |
| PEG Mn: 1500 | 4 | 32.74 | 0.22 |
| PEG Mn: 1500 | 6 | 31.88 | 1.30 |
| PEG Mn: 1500 | 11 | 33.48 | 0.29 |

Further formulations were prepared and tested. 3 replicates of 13 mm disc-shaped, 0.5 g tablets were compacted under 60 kN. All formulas consist of 23.8% 3-NOP, 28.6% silica, and 47.6% ethyl cellulose. Tablets were then coated with 60-80 wt % of the corresponding coating material. Control tablet (CTRL) is uncoated. "R" denotes replicate number. CAP coating solution was 18 wt % in 70% ethanol/water. Cellulose acetate (CA) coating was 6 wt % in 70% ethanol/ethyl acetate with an additional 5 wt % triethyl citrate, 5 wt % propylene glycol, and 5 wt % N-methyl-2-pyrollidone. The release profiles were analyzed at 1, 4, 8, 11, and 15 days, as summarized in Table 4.

TABLE 4

3-NOP release profile of coated tablets over 15 days.
Total concentration of 3-NOP is listed in mM.

| CAP R1 | 25.74 | 47.79 | 59.39 | 61.05 | 59.68 |
|---|---|---|---|---|---|
| CAP R2 | 18.72 | 43.71 | 52.56 | 53.74 | 53.37 |
| CAP R3 | 23.12 | 50.66 | 57.23 | 59.23 | 58.75 |
| AVG | 22.53 | 47.39 | 56.39 | 58.01 | 57.26 |
| STD | 3.54 | 3.49 | 3.49 | 3.81 | 3.41 |
| CA R1 | 50.90 | 75.98 | 73.80 | 66.97 | 61.48 |
| CA R2 | 71.29 | 78.41 | 73.11 | 66.66 | 60.18 |
| CA R3 | 63.86 | 69.38 | 65.56 | 61.28 | 57.00 |
| AVG | 62.01 | 74.59 | 70.82 | 64.97 | 59.55 |
| STD | 10.32 | 4.67 | 4.57 | 3.20 | 2.31 |
| CTRL R1 | 45.80 | 80.64 | 80.33 | 73.64 | |
| CTRL R2 | 45.80 | 84.41 | 83.39 | 76.22 | 69.25 |
| CTRL R3 | 45.80 | 77.15 | 75.92 | 70.11 | 62.74 |
| AVG | 45.80 | 80.73 | 79.88 | 73.32 | 66.00 |
| STD | 0.00 | 3.63 | 3.76 | 3.07 | 4.60 |

Coated Tablets

All formulation percentages are based on weight. 3 replicates of 13 mm disc-shaped, 0.5 g tablets were compacted under 60 kN. All formulas consist of 23% 3-NOP, 30% silica, and 47% ethyl cellulose. Tablets were then coated with 60-80 wt % of the corresponding coating material. Control tablet (CTRL) is uncoated. V1 coating solution was 20 wt % cellulose acetate Mn: 50000 in 70% acetone/ethyl acetate with BYK coating additives. V2 coating solution was 20 wt % in 70% acetone/ethyl acetate cellulose acetate Mn: 50000 with BYK coating additives. Ethyl cellulose coating solution was 20 wt % in 70% ethanol/water with 15 wt % triacetin. CAP coating solution was 18 wt % in 70% ethanol/water with 10 wt % propylene glycol. The 3-NOP release profile of the coated tablets over 18 days is shown in Table 5.

TABLE 5

3-NOP release profile of coated tablets over 18 days.
Total concentration of 3-NOP is listed in mM.

| | Time | | | | |
|---|---|---|---|---|---|
| | 1 | 5 | 8 | 12 | 18 |
| V1 R1 | 33.04 | 70.32 | 70.57 | 66.04 | 60.88 |
| V1 R2 | 57.54 | 77.54 | 77.42 | 72.65 | 67.44 |
| V1 R3 | 61.42 | 71.21 | 70.08 | 65.71 | 61.19 |
| AVG | 50.67 | 73.02 | 72.69 | 68.13 | 63.17 |
| STD | 15.39 | 3.93 | 4.10 | 3.91 | 3.70 |
| V2 R1 | 31.15 | 66.47 | 65.62 | 61.03 | 56.78 |
| V2 R2 | 32.55 | 66.81 | 67.61 | 63.67 | 59.55 |
| V2 R3 | 53.59 | 69.37 | 71.28 | 67.53 | 63.01 |
| AVG | 39.10 | 67.55 | 68.17 | 64.08 | 59.78 |
| STD | 12.57 | 1.59 | 2.87 | 3.27 | 3.12 |
| EC R1 | 17.99 | 39.67 | 45.39 | 47.12 | 50.00 |
| EC R2 | 15.84 | 38.15 | 43.53 | 45.83 | 49.27 |
| EC R3 | 21.21 | 52.28 | 58.64 | 60.42 | 63.56 |
| AVG | 18.35 | 43.37 | 49.19 | 51.13 | 54.28 |
| STD | 2.70 | 7.75 | 8.24 | 8.08 | 8.05 |
| CAP R1 | 24.07 | 57.62 | 63.10 | 69.28 | 68.61 |
| CAP R2 | 23.24 | 56.30 | 61.85 | 60.67 | 59.42 |
| CAP R3 | 37.58 | 63.57 | 71.80 | 69.89 | 70.48 |
| AVG | 28.30 | 59.17 | 65.58 | 66.61 | 66.17 |
| STD | 8.05 | 3.87 | 5.42 | 5.15 | 5.92 |
| CTRL R1 | 61.62 | 97.29 | 89.52 | 81.26 | 74.20 |
| CTRL R2 | 45.40 | 82.69 | 79.42 | 73.16 | 67.07 |
| CTRL R3 | 53.75 | 83.30 | 76.77 | 70.18 | 64.12 |
| AVG | 53.59 | 87.76 | 81.90 | 74.87 | 68.47 |
| STD | 8.11 | 8.26 | 6.73 | 5.74 | 5.18 |

Bilayer Coated Tablets

All formulation percentages are based on weight. 3 replicates of 13 mm disc-shaped, 0.5 g tablets were compacted under 60 kN. All formulas consist of 15% 3-NOP, 20% silica, and 65% ethyl cellulose. Bilayer coatings were applied with ~10 wt % of the first coating material and ~20 wt % of the second coating material. CAP/EC denoted first and second coating material. The 3-NOP release profile of bilayer coated tablets over 27 days is shown in Table 6.

TABLE 6

3-NOP release profile of bilayer coated tablets over 27 days. Total concentration of 3-NOP is listed in mM.

| | Time (days) | | | | | | | | |
|---|---|---|---|---|---|---|---|---|---|
| | 1.25 | 2.5 | 5.5 | 8 | 10 | 14 | 17 | 21 | 27 |
| CAP/EC R1 | 6.27 | 8.80 | 15.97 | 18.49 | 20.41 | 24.15 | 24.59 | 24.46 | 26.21 |
| CAP/EC R2 | 4.39 | 7.77 | 15.50 | 17.78 | 19.54 | 22.90 | 23.44 | 23.74 | 25.94 |
| CAP/EC R3 | 5.63 | 8.43 | 15.44 | 17.84 | 19.29 | 20.36 | 20.94 | 21.18 | 22.65 |
| AVG | 5.43 | 8.33 | 15.64 | 18.04 | 19.75 | 22.47 | 22.99 | 23.13 | 24.93 |
| STD | 0.96 | 0.52 | 0.29 | 0.39 | 0.59 | 1.93 | 1.87 | 1.73 | 1.98 |
| EC/CAP R1 | 9.75 | 14.58 | 22.35 | 23.09 | 23.76 | 26.40 | 26.04 | 26.12 | 26.82 |
| EC/CAP R2 | 10.72 | 17.13 | 24.89 | 26.10 | 26.78 | 29.51 | 28.89 | 28.52 | 29.31 |
| EC/CAP R3 | 9.84 | 15.34 | 22.33 | 24.08 | 25.21 | 28.03 | 27.91 | 27.56 | 28.17 |
| AVG | 10.10 | 15.68 | 23.19 | 24.42 | 25.25 | 27.98 | 27.61 | 27.40 | 28.10 |
| STD | 0.54 | 1.31 | 1.47 | 1.54 | 1.51 | 1.56 | 1.45 | 1.21 | 1.25 |
| CTRL R1 | 26.11 | 28.76 | 36.26 | 37.49 | 36.75 | 35.77 | 33.69 | 31.26 | 32.66 |
| CTRL R2 | 26.12 | 28.43 | 38.45 | 39.57 | 38.58 | 37.45 | 34.91 | 32.16 | 33.30 |
| CTRL R3 | 25.23 | 29.94 | 40.65 | 41.23 | 45.02 | 42.91 | 39.10 | 27.92 | −2.04 |
| AVG | 25.82 | 29.05 | 38.45 | 39.43 | 40.12 | 38.71 | 35.90 | 30.45 | 21.31 |
| STD | 0.51 | 0.79 | 2.19 | 1.87 | 4.34 | 3.73 | 2.84 | 2.24 | 20.22 |

Adsorbent Study

Various adsorbents were assessed for potential binding affinity and adsorptive capacity of 3-NOP. Activated carbon/charcoal and silica were identified as the most suitable adsorbents based on their high binding affinity and adsorptive capacity.

Briefly, 0.2 g of adsorbent was added to 4 mL of 2.5% 3-NOP/H2O stock solution or 10 mL of 1% 3-NOP/H$_2$O stock solution. The solution was then placed in an ultrasonic bath for ~4 hr and then allowed to equilibrate over 24 h. All materials were purchased from Sigma-Aldrich and used as received. After 24 h, adsorbents were tested for their binding affinity and adsorptive capacity by looking at the reduction of 3-NOP concentration via HPLC at 230 nm.

Figure 7:
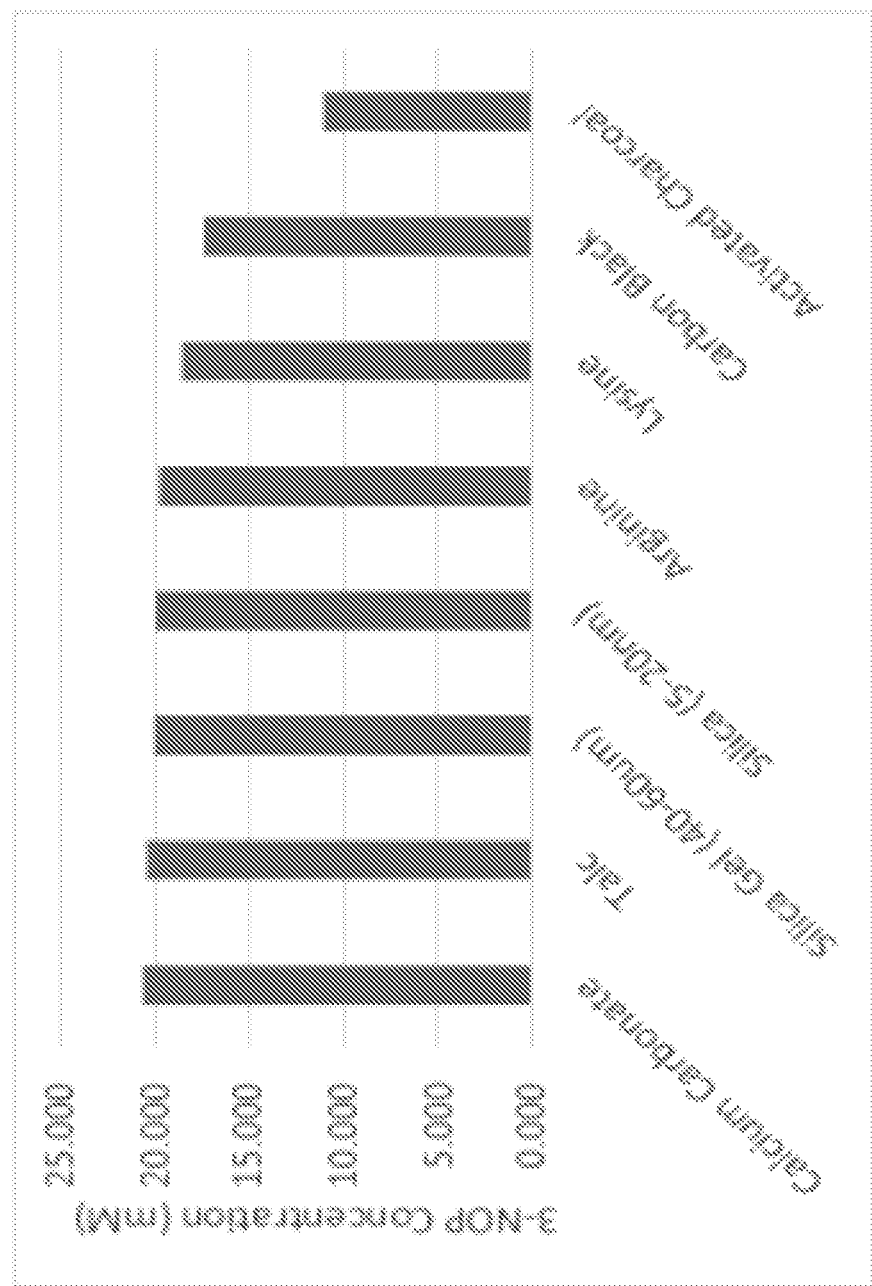
FIG. 7 shows 3-NOP concentration (mM) v. adsorbent (~20 mM stock solution).

The following adsorbents were tested and integrated areas were converted to mM concentrations of 3-NOP based on calibration standards of known 3-NOP concentration in distilled water, as seen in Table 7. FIG. 7 is graph showing the concentration of 3-NOP (mM) v. adsorbent (20 mM stock solution).

TABLE 7

Change in concentration v. control of 0.2 g of adsorbent in 4 mL of 2.5% 3-NOP/H2O.

| Adsorbent | 3-NOP concentration (mM) |
|---|---|
| Control | 20.649 |
| Calcium Carbonate | 20.649 |
| Talc | 20.463 |
| Silica Gel (40-60 um) | 20.043 |
| Silica (5-20 nm) | 19.920 |
| Arginine | 19.782 |
| Lysine | 18.583 |
| Carbon Black | 17.422 |
| Activated Charcoal | 11.063 |

Figure 8:
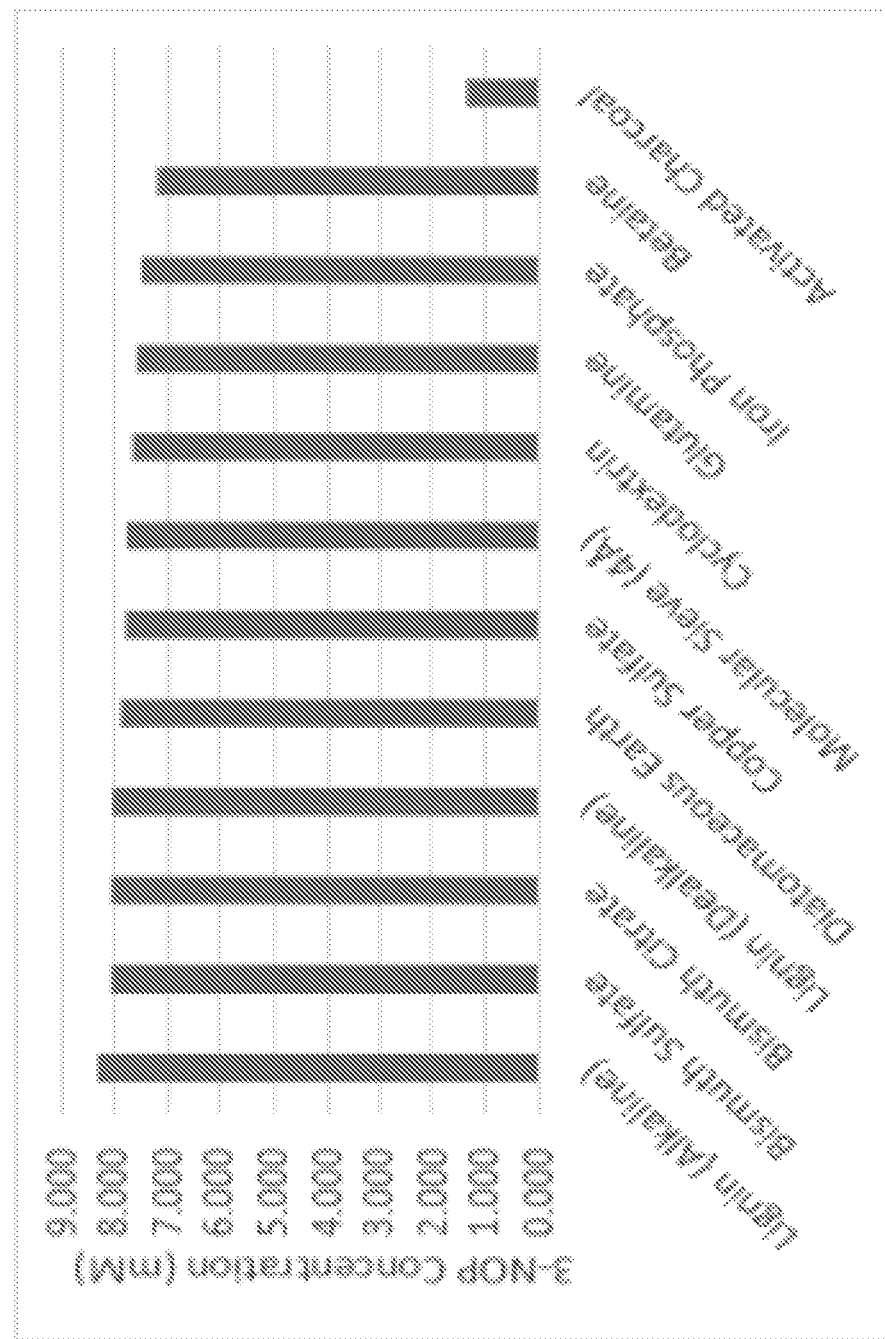
FIG. 8 shows 3-NOP concentration (mM) v. adsorbent (~8 mM stock solution).

Table 8 shows the change in concentration v. control of 0.2 g of adsorbent in 10 mL of 1% 3-NOP/H2O, and FIG. 8 shows 3-NOP concentration (mM) v. adsorbent (~8 mM stock solution).

TABLE 8

Change in concentration v. control of 0.2 g of adsorbent in 10 mL of 1% 3-NOP/H2O.

| Adsorbent | 3-NOP concentration (mM) |
|---|---|
| Control | 8.258 |
| Lignin (Alkaline) | 8.326 |
| Bismuth Sulfate | 8.079 |
| Bismuth Citrate | 8.072 |
| Lignin (Dealkaline) | 8.056 |
| Diatomaceous Earth | 7.895 |
| Copper Sulfate | 7.814 |
| Molecular Sieve (4 Å) | 7.771 |
| Cyclodextrin | 7.676 |
| Glutamine | 7.588 |
| Iron Phosphate | 7.503 |
| Betaine | 7.202 |
| Activated Charcoal | 1.358 |

Activated carbon shows strong binding affinity for 3-NOP filtering ~45 wt % in concentrated (20 mM) conditions with ~80 wt % in more dilute concentrations (8 mM). It appears that the adsorbent pore size should be greater than 4 Å for adsorption of 3-NOP. Mesoporous adsorbents with high surface area such as silica and activated carbon show high adsorptive capacity with no visible wetting seen until ~75 wt %. Layer-by-Layer Polyelectrolytes Coatings Formulated tablets containing 3-NOP, an adsorbent, and a binder can be coated with sequential layers of oppositely charged polyelectrolytes. While not being bound by theory, it is believed that ionic crosslinking between the layers can result in a controlled release of 3-NOP out of the tablets. Examples of polyelectrolyte pairs that can be used include polyglutamic acid and polylysine, polyallylamine hydrochloride and polyacrylic acid, and polyallylamine hydrochloride and polystyrene sulfonate. An exemplary formulated tablet includes an adsorbent of silica, arginine, lysine, and activated charcoal (30-45%) and a binder of ethyl cellulose and hydroxypropyl cellulose (40-55%).

TABLE 9

Formulation examples of 3-NOP tablets.
Tablet weight varied from 0.2-0.5 g.
Tablet Formulation

| Adsorbent | Part per formulation (wt %) | Binder | Part per formulation (wt %) |
|---|---|---|---|
| Silica, Arginine, Lysine, Activated Charcoal | 30-45 | Ethyl Cellulose, Hydroxypropyl Cellulose | 40-55 |

The release data of 3-NOP tablets coated with multilayers of some polyelectrolytes is shown in Table 10.

TABLE 10

Release (%) of 3-NOP out of tablets formulated with 15% 3-NOP, 30% silica, and 55% ethyl cellulose. Weight of tablets~0.5 g. Calculations are based on a comparison to control tablets with no coating.

| | Release Compared to Control Tablets (%) | | | | | | | |
|---|---|---|---|---|---|---|---|---|
| PE Pair | Day 1 | Day 3 | Day 6 | Day 8 | Day 14 | Day 16 | Day 21 | Day 30 |
| PLK20 + PRE20 | 58.1 | 56.6 | 61.3 | 62.6 | 64.7 | 63.6 | 63.8 | 63.2 |
| PAH + PAA | 61.5 | 62.5 | 67.1 | 70.2 | 70.4 | 71.4 | 71.7 | 71.6 |
| PAH + PSS | 61 | 66.5 | 74.7 | 76 | 77.5 | 76.6 | 76.7 | 74.8 |

3-NOP to Adsorbent Ratio Study

Optimal loading of 3-NOP onto adsorbents was determined by varying ratios of 3-NOP to adsorbent. 3-NOP and adsorbent were speed mixed at 2000 rpm for 1 min at the following ratios by weight: 1:1.5, 1:2, 1:2.5. The adsorbed 3-NOP powder mixture was then placed in distilled water at 1% 3-NOP loading. The solution was allowed to equilibrate for 24 hr and then an aliquot was taken for HPLC to determine the reduction in 3-NOP concentration. Table 11 shows the average integrates are of 3-NOP in solution at various adsorbent raios.

TABLE 11

Average integrated area of 3-NOP in solution at varying 3-NOP:adsorbent ratios.

| | 1:1.5 | | 1:2 | | 1:2.5 | |
|---|---|---|---|---|---|---|
| 3-NOP: Adsorbent | Average Integrated Area | Standard Deviation | Average Integrated Area | Standard Deviation | Average Integrated Area | Standard Deviation |
| 3-NOP | 2566.4 | 51.3 | 2566.4 | 51.3 | 2566.4 | 51.3 |
| Silica | 2499.4 | 293.2 | 2321.9 | 99.3 | 2340.9 | 30.3 |
| Activated charcoal | 1751.2 | 29.6 | 1581.9 | 8.5 | 1403.7 | 14.5 |
| Lysine | 2336.2 | 61.7 | 2308.9 | 23.9 | 2266.6 | 56.1 |
| Arginine | 2406.0 | 113.2 | 2372.8 | 61.2 | 2435.2 | 230.2 |
| Glutamic acid | 2445.9 | 149.9 | 2452.5 | 78.9 | 2446.3 | 85.0 |

Higher ratios of activated carbon to 3-NOP result in higher adsorptive capacity. At ratio of 1:2.5 an adsorption capacity of ~45% is observed and at a ratio of 1:1.5 an adsorption capacity of ~30% is observed.

Activated Carbon Tablets

Based on the 3-NOP:adsorbent ratio study, the same ratios were tested for tablet integrity, friability, porosity, etc to determine the optimal 3-NOP loading. 500 mg, 13 mm tablets were compacted under 60 kN.

High ratios of activated carbon (1:2.5 3-NOP:adsorbent) resulted in tablets that absorb more water and coating solutions. This water/solvent absorption of non-wetted charcoal causes difficulty in producing uniform, defect free coatings. High loadings of activated charcoal >25% in tablets result in poor tablet integrity characterized by loss in hardness, increased porosity, tablet spilling, and poor shape retention. The preferred loading for tablets with poor disintegration was 1:1.5 3-NOP:adsorbent.

Figure 9:
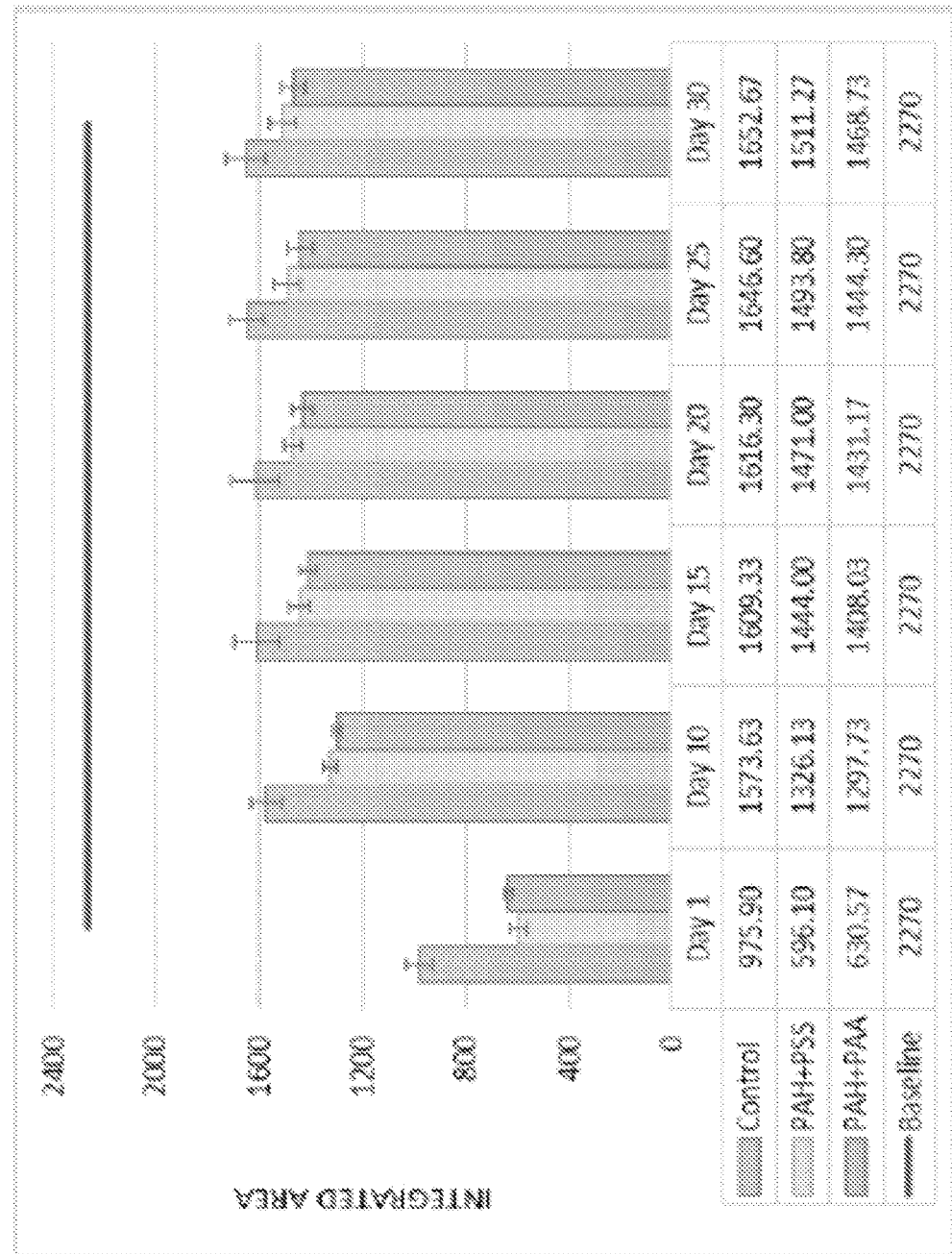
FIG. 9 shows exemplary multilayer polyelectrolyte coatings of 15% activated carbon tablets.

FIG. 9 shows a multilayer tablet formulation above consisting of 10 wt % 3-NOP, 15 wt % activated carbon, and 75 wt % ethyl cellulose. The first day release of coated tablets is ~40% less than uncoated tablets and after 30 days, ~30% 3-NOP remains adsorbed on activated carbon.

Figure 10:
FIG. 10 shows exemplary multilayer polyelectrolyte coatings of 25% activated carbon tablets.

FIG. 10 shows a multilayer tablet formulation consisting of 10 wt % 3-NOP, 25 wt % activated carbon, and 75 wt % ethyl cellulose. After 30 days, ~50% 3-NOP remains adsorbed on activated carbon. These adsorptive capacities are in-line with what was observed during the 3-NOP: adsorbent ratio study.

Figure 11:
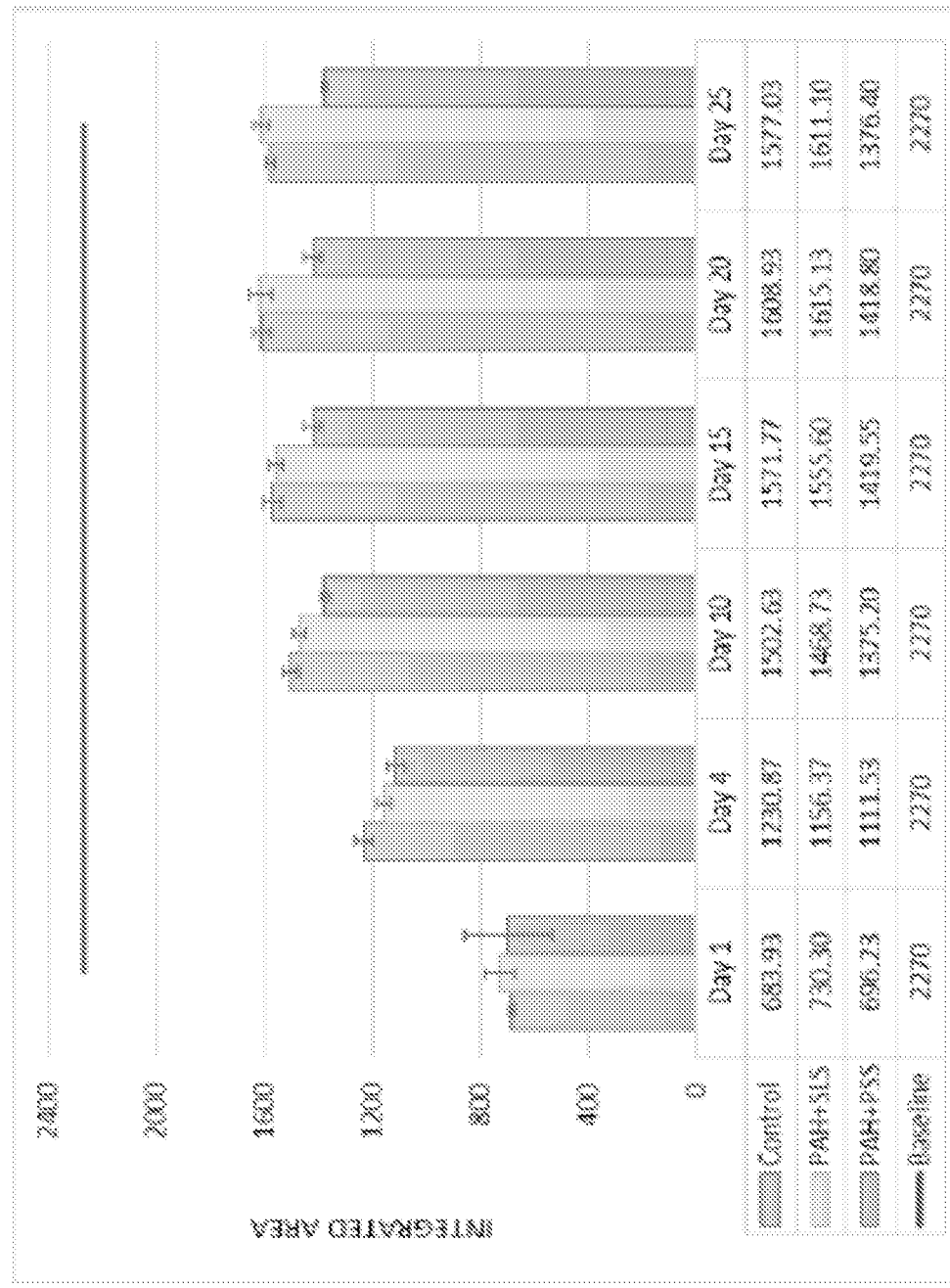
FIG. 11 shows exemplary multilayer polyelectrolyte coatings of 15% activated carbon tablets with 5% sodium lignosulfonate.

FIG. 11 shows a multilayer formulation consisting of 10 wt % 3-NOP, 15 wt % activated carbon, 5 wt % sodium lignosulfonate, and 70 wt % ethyl cellulose. The addition of 5 wt % sodium lignosulfonate improves coating adhesion to the tablet resulting in ~30% reduction in the first day 3-NOP release. Over time, the release rate remains similar to previous formulations with a residual 30% 3-NOP remaining adsorbed to activated carbon.

Figure 12:
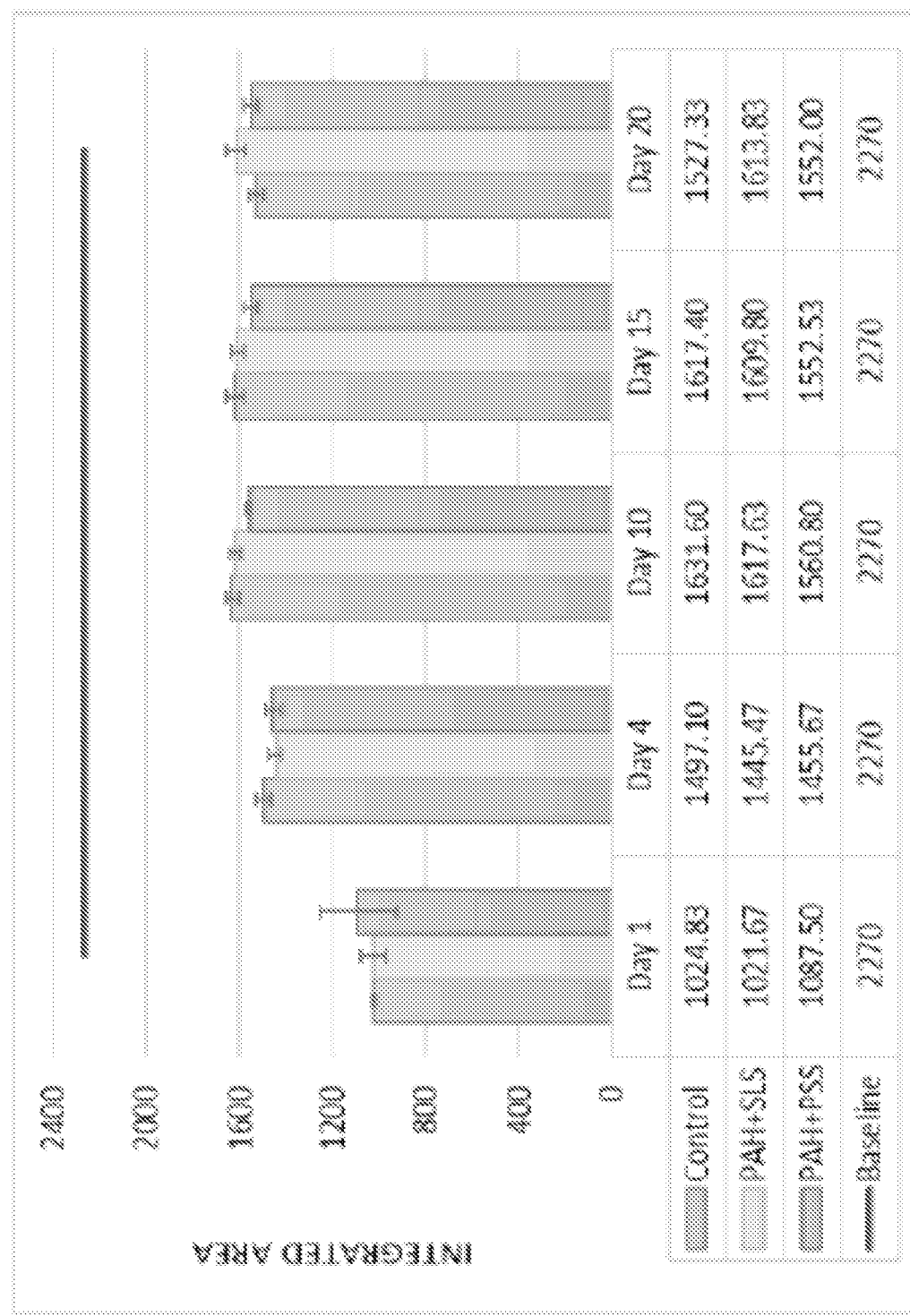
FIG. 12 shows exemplary multilayer polyelectrolyte coatings of 15% activated carbon with 5% hydroxypropyl cellulose.

FIG. 12 shows a multilayer formulation consisting of 10 wt % 3-NOP, 15 wt % activated carbon, 5 wt % hydroxypropyl cellulose, and 70 wt % ethyl cellulose. The addition of 5 wt % hydroxypropyl cellulose, a hydrophilic water-soluble binder, results in increased release between day 4 and day 10. After 30 days, ~30% 3-NOP remains adsorbed to activated carbon.

Silica v. Activated Carbon Controls to Assess Binding Affinity of 3-NOP

Various control experiments were conducted to confirm the adsorbed 3-NOP to activated carbon after 30 days. Activated carbon was compared to silica as preferred adsorbents.

500 mg of 1:1.5 3-NOP:adsorbent were speed mixed at 2000 rpm for 1 min. The resulting powder mixture was placed in 10 mL of distilled water and 10 mL of acetonitrile (ACN) separately. The solutions were placed in a sonic bath for ~5 hr, removed, and allowed to equilibrate for 24 hr.

Aliquots were filtered through a 0.22 um PTFE filter, and taken for HPLC to measure the 3-NOP concentration in solution.

The same trend was observed in the adsorbent study. However, 3-NOP is recoverable by washing the activated carbon with acetonitrile or a similar organic solvent with high 3-NOP solubility (ie. ethanol, acetone, ethyl acetate, tetrahydrofuran, chloroform).

TABLE 12

Silica powder release v. activated carbon release in distilled water and acetonitrile.

|  | 24 hr in H2O Integrated Area | 24 hr in ACN Integrated Area |
|---|---|---|
| Si-1 | 8415.7 | 8847 |
| Si-2 | 8507.3 | 8822.2 |
| Average | 8461.5 | 8834.6 |
| AC-1 | 4940.8 | 8103.9 |
| AC-2 | 5577.5 | 8082.8 |
| Average | 5259.2 | 8093.4 |

Figure 13:
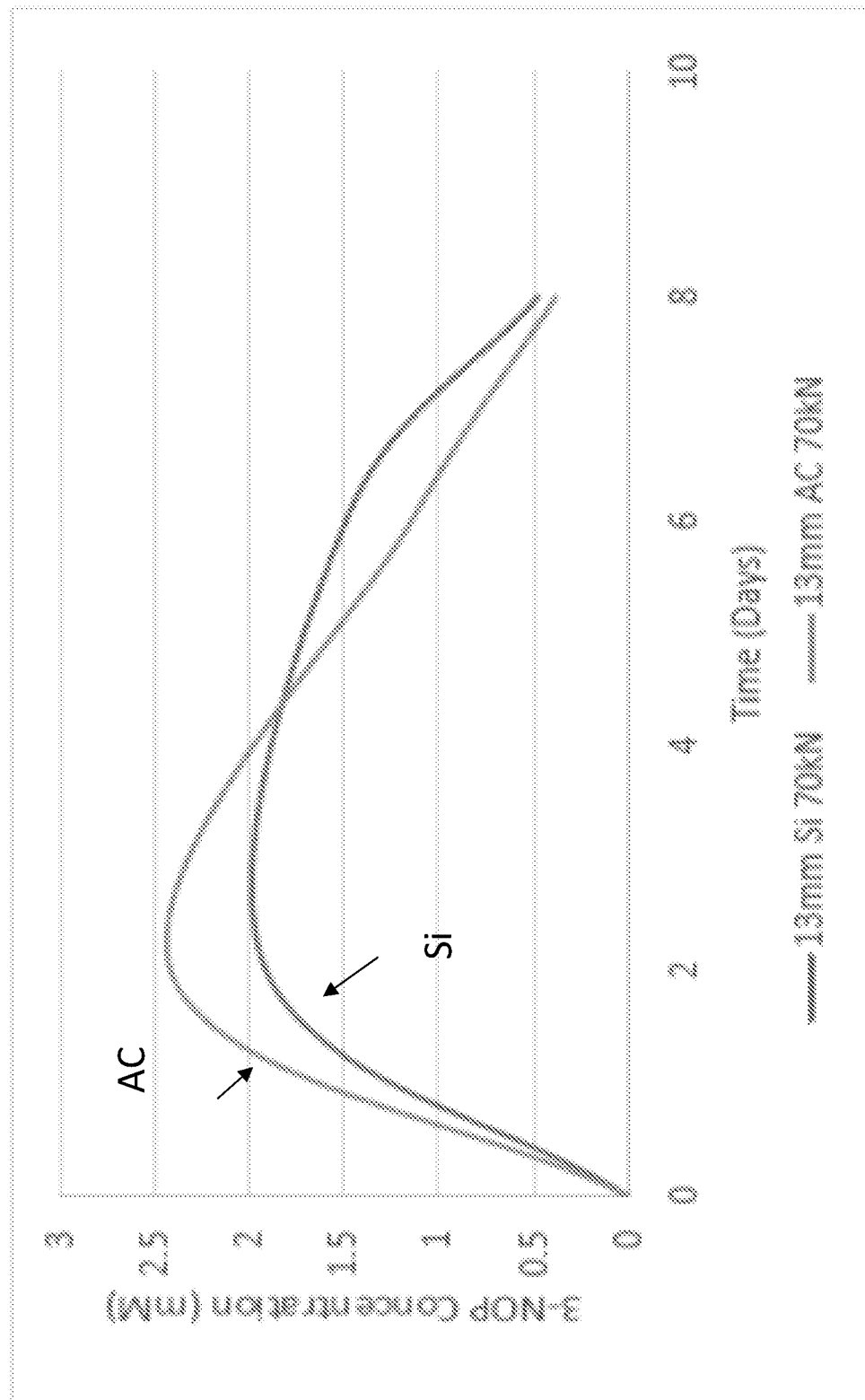
FIG. 13 is a graph showing the release profiled of a silica v. activated carbon adsorbent.

After 24 hr in water, less than 5 wt % 3-NOP remained adsorbed to silica compared to the powder mix placed in acetonitrile. After 24 hr in water, ~35 wt % 3-NOP remained adsorbed to activated carbon compared to the powder mix placed in acetonitrile. By washing the activated carbon in acetonitrile, the adsorbed 3-NOP can be recovered in solution proving that the remaining 30-50% 3-NOP that is seen in FIGS. 4-7 remains adsorbed. Further studies need to be conducted to determine the driving forces for 3-NOP desorption from activated carbon under different environmental conditions to utilize adsorptive capacity of activated carbon. This study also confirms that from previous tablet formulations, diffusion is the primary driver for 3-NOP release of unbound 3-NOP. This can be seen by very similar release profiles between silica-based adsorbent tablets and activated carbon-based adsorbent tablets. FIG. 13 compares a silica-based tablet and activated carbon-based tablet over 8 days. Small differences in release profiles could be due to differences in porosity between tablets using silica or activated carbon.

Compounding of 3-NOP

3-NOP was compounded with a variety of matrix materials using a DSM Xplore MC15 conical twin-screw extruder. The extrudate was pelletized and used as is or further compression molded into tablets as a suitable 3-NOP extended-release form.

3-NOP was adsorbed onto the corresponding adsorbent and speed mixed with binder prior to compounding is a DSM Xplore MC15 conical twin-screw extruder at 100 C and 50 rpm. The strand was then pelletized, heated, and molded into a 13 mm disc-shaped tablet using a carver press under 40 kN of compaction force. Formula consists of 8.3% 3-NOP, 25.0% arginine, 66.7% CAPA 6800.

TABLE 13

3-NOP release profile of compounded tablets over 24 days. Total concentration of 3-NOP is listed in mM.

|  | Time | | | | | | |
|---|---|---|---|---|---|---|---|
|  | 1 | 3 | 7 | 10 | 14 | 20 | 24 |
| Arg R1 | 8.97 | 16.37 | 22.55 | 23.42 | 24.11 | 23.07 | 24.56 |
| Arg R2 | 12.49 | 15.85 | 20.43 | 21.45 | 21.60 | 19.33 | 19.97 |
| Arg R3 | 9.90 | 17.78 | 24.52 | 24.50 | 24.36 | 22.60 | 22.33 |
| AVG | 10.45 | 16.67 | 22.50 | 23.13 | 23.36 | 21.67 | 22.29 |
| STD | 1.82 | 1.00 | 2.04 | 1.55 | 1.52 | 2.04 | 2.29 |

Formulas consists of 11.1% 3-NOP, 13.9% silica, 75.0% CAPA 6800 denoted "11PCL" and 19.4% 3-NOP, 24.2% silica, 56.5% CAPA 6800 denoted "19PCL."

TABLE 14

3-NOP release profile of compounded tablets over 24 days. Total concentration of 3-NOP is listed in mM.

|  | Time | | | | |
|---|---|---|---|---|---|
|  | 1 | 3 | 7 | 13 | 17 |
| 11PCL R1 | 9.79 | 18.77 | 24.31 | 29.15 | 27.93 |
| 11PCL R2 | 10.34 | 19.81 | 24.99 | 30.02 | 29.49 |
| 11PCL R3 |  | 19.05 | 22.51 | 27.14 | 26.95 |
| AVG | 10.06 | 19.21 | 23.94 | 28.77 | 28.12 |
| STD | 0.39 | 0.54 | 1.28 | 1.48 | 1.28 |
| 19PCL R1 | 23.55 | 40.56 | 49.99 | 55.00 | 3.48 |
| 19PCL R2 | 24.19 | 40.59 | 51.03 | 53.46 | 51.64 |
| 19PCL R3 | 25.05 | 42.76 | 52.21 | 57.93 | 55.77 |
| AVG | 24.26 | 41.30 | 51.08 | 55.47 | 36.96 |
| STD | 0.75 | 1.26 | 1.11 | 2.27 | 29.07 |

Compounded Polyelectrolyte Complexes for Extended Release of 3-NOP

Solid polyelectrolyte complexes can be processible when plasticized with aqueous electrolytes to act as a matrix for 3-NOP molecules. An example of a polyelectrolyte pair for compounding is polydiallyldimethylammonium chloride (PDADMAC), as a cationic polyelectrolyte, and polystyrene sulfonate (PSS), as an anionic polyelectrolyte. At no salt conditions, the complex is brittle and not ideal for processing and the addition of salt, such as sodium chloride, can help with the plasticization and further processing. A trial formulation used for compounding includes mixing of equal charge stoichiometry of PDADMAC and PSS solutions with a concentration of 100 mM, with respect to each polymer, and a total volume of 200 mL (as per preparation method described in ACS Appl. Mater. Interfaces 2015, 7, 895-901). The polyelectrolyte complex can be separated, removed from the supernatant phase, and soaked in salt water with a concentration of 1M for 24 h. The polyelectrolyte complex should be decanted and ready for compounding. A typical formulation used for compounding is summarized in Table 13.

TABLE 15

Compounding formulation with polyelectrolyte complexes for extended release of 3-NOP. Total materials used 20 g. 3-NOP was mixed with arginine (as in solid powder) overnight at 30 C. PEC Compounding Formulation

| 3-NOP Complex | Part per formulation (wt %) | PEC Complex | Part per formulation (wt %) |
|---|---|---|---|
| 3-NOP:Arginine (ratio 1:3, wt %) | 25 | PDADMAC:PSS (Equimolar with respect to the monomer) | 75 |

Table 16 shows release (%) of 3-NOP out of compounded PEC formulated as per Table 6. The compounded PECs were cut into 5-10 mm pellets and soaked in water (10 mL) for the release study.

TABLE 16

| Release (%) | | | |
|---|---|---|---|
| Day 1 | Day 4 | Day 6 | Day 12 |
| 22.4 | 34.4 | 35 | 35.7 |

Compounded Pellets

Figure 15:
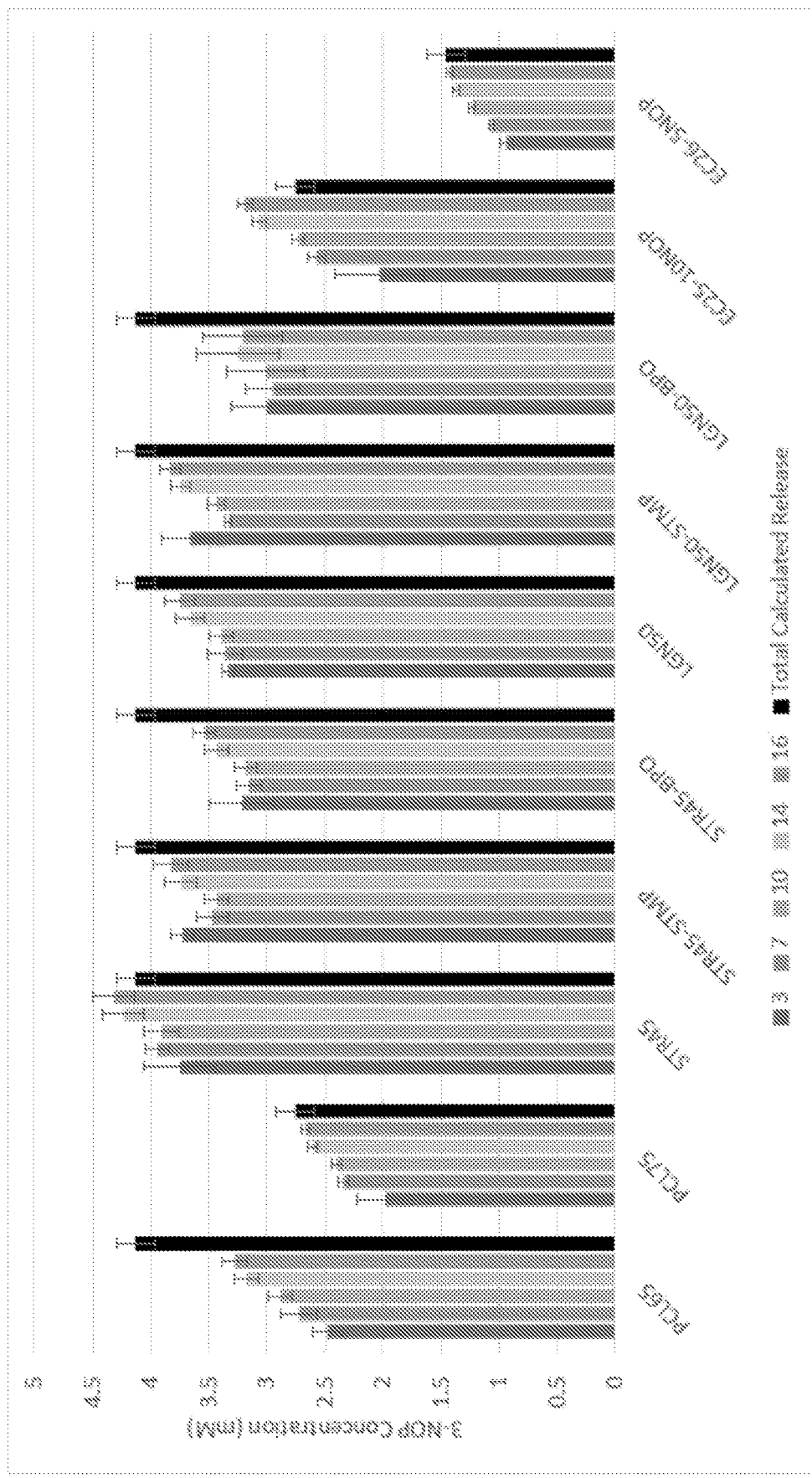
FIG. 15 is a bar graph showing 3-NOP release in mM for exemplary polycaprolactone-based formulations.

3-NOP was adsorbed onto the corresponding adsorbent and speed mixed with binder prior to compounding is a DSM Xplore MC15 conical twin-screw extruder at temperatures of 110-130 C and 100 rpm. The extrudate was then pelletized forming ~2 mm pellets. Material suppliers are listed in Table 15. Polybutylene succinate grades FZ71, FZ91, FD92 were supplied by Mitsubishi Chemical. Polycaprolactone-based formulations are summarized in the Table in FIG. 14. FIG. 15 shows 3-NOP release in mM for polycaprolactone-based formulations.

TABLE 18

| Polybutylene succinate-based formulations | | | | |
|---|---|---|---|---|
| | Code | | | |
| | 65FZ71 | 65FZ91 | 65FD92a | 65FD92b |
| | Material | | | |
| Polybutylene succinate | 65.0% | 65.0% | 65.0% | 65.0% |
| Activated charcoal | 20.0% | 20.0% | 20.0% | 20.0% |
| 3-NOP | 15.0% | 15.0% | 15.0% | 15.0% |
| | On total solids | | | |
| Glycerol monooleate | 0.5% | 0.5% | 0.5% | 0.0% |
| Compounding Temperature | 120 C. | 120 C. | 130 C. | 110 C. |

Figure 16:
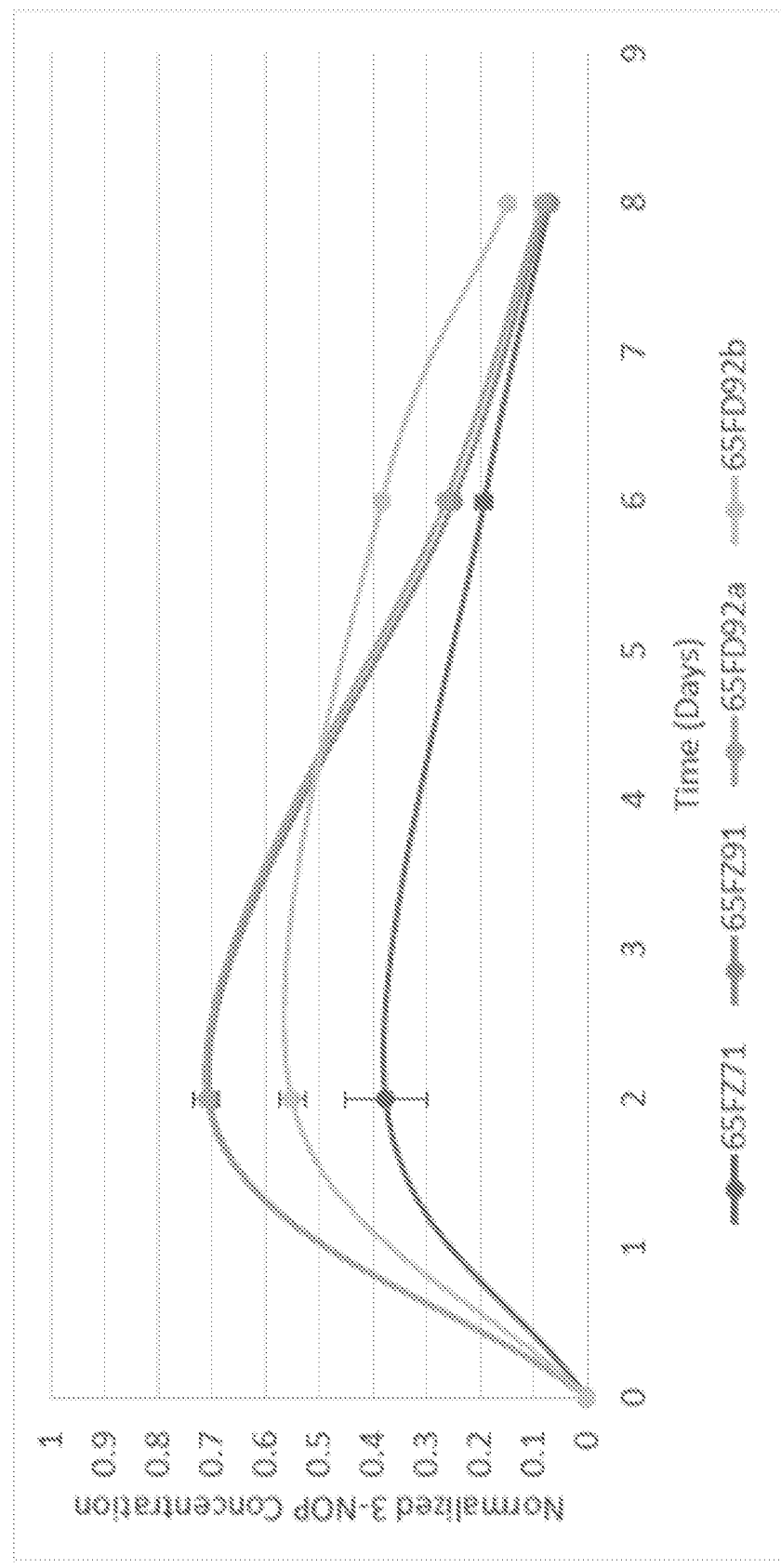
FIG. 16 is a graph showing normalized 3-NOP concentration v. release time in days of exemplary polybutylene succinate-based formulations.

FIG. 16 is chart showing the normalized 3-NOP concentration v. Release time in days of polybutylene succinate-based formulations. Lower 3-NOP loadings (<10%) have a less pronounced burst release over the first 7 days of monitored release. Glycerol monooleate was identified at a potent processing aid at loadings <1%. High levels <25 wt % activated carbon can easily be processed unlike silica which leads to high viscosity and screw torque. Cross-linked systems show slower release in comparison to un-cross-linked systems. High shear conditions of compounding appear to destroy activated carbon structure and adsorption capacity is lost.

Microcapsules for the Encapsulation of 3-NOP

Polyelectrolyte complexes (PECs) are used to form microcapsules and encapsulate 3-NOP. PECs are formed through attractive forces such as ionic interactions, hydrogen bonding, hydrophobic, and pi-interactions between the polyelectrolytes. Polyelectrolytes are polymers with ionic groups bonded to counter ions and can dissociate in a solution to make positively or negatively charged polymers. Herein, PEC microcapsules refer to interconnecting networks of polyelectrolytes formed upon the interaction between oppositely charged polymers.

Examples of polyelectrolytes used in this invention include synthetic polyelectrolytes such as polystyrene sulfonate (PSS), polyacrylic acid (PAA), and polyallylamine hydrochloride (PAH). Further examples include naturally occurring polyelectrolytes such as chitosan and alginate or ionic biopolymers such as proteins, enzymes, and charged polypeptides.

Examples of Polyelectrolytes (charged polymers with positively or negatively charged repeating units) Used:

Synthetic Polyelectrolytes
  Polystyrene sulfonate (PSS), molecular weight ~200,000 Da, Sigma Aldrich
  Sodium Lignosulfonate (SLS), molecular weight ~52000 Da, Sigma Aldrich
  Polyethyleneimine (PEI), molecular weight ~2000 Da, Polysciences
  Polyallylamine hydrochloride (PAH), molecular weight ~17,500 Da, Sigma Aldrich Commercially Available Peptide Sequences
  Poly (L-lysine) (PLK10), degree of polymerization: 10, molecular weight: 1600 Da, Alamanda Polymers
  Poly (L-lysine) (PLK20), degree of polymerization: 20, molecular weight: 3300 Da, Alamanda Polymers
  Poly (L-arginine) (PLR$^{10}$), degree of polymerization: 10, molecular weight: 1900 Da, Alamanda Polymers Examples of Crosslinker Used
  Glutaraldehyde, 25% solution in water, Sigma Aldrich
  EDC (1-ethyl-3-(3-dimethylaminopropyl) carbodiimide hydrochloride), Thermo Fisher.

PEC Microcapsules Preparation

Equal stoichiometry of oppositely charged polyelectrolytes is sequentially added to water or water-3-NOP solutions followed by vortexing for 10 s, after the addition of each component, to form PEC microcapsules. Some samples are chemically crosslinked (glutaraldehyde is an example of the crosslinker used). The PEC microcapsules may also be formed with non-stoichiometric ratios of polyelectrolytes. While stoichiometric ratios of polyelectrolytes provide almost a neutral microcapsule, microcapsules prepared with non-stoichiometric ratios are positively or negatively charged. All polyelectrolyte solutions are prepared in water and pH adjusted. The concentration of solutions is based on the monomer charge. The stock solution of 3-NOP is prepared in water with a concentration of 100 mM and pH adjusted to 8.

High-performance liquid chromatography (HPLC) is used to determine the concentration of 3-NOP in PEC microcapsules and calculate the release of 3-NOP from the microcapsules. Samples are centrifuged to separate the supernatant phase from the complex phase. The supernatant phase is then removed carefully by using a micropipette and transferred to a 2 mL glass vial for further analysis. The 3-NOP release of some PEC microcapsules prepared at neutral pH conditions and after 96 h of preparation is summarized in Table 17.

TABLE 19

3-NOP release (%) from the PEC microcapsules. Samples are prepared with a 3-NOP concentration of 100 μM. Final pH solution ~7. K, L, F, and E refer to lysine, leucine, phenylalanine, and glutamic acid, respectively. PSS refers to polystyrene sulfonate.

| Polyelectrolyte Pair | Release (%) at 96 h timepoint | 3-NOP Concentration in Microcapsules (μM) |
|---|---|---|
| (KKLF)$_3$ + (EELF)$_3$ | 63 | 37 |
| (KKLF)$_3$ + PSS | 64 | 36 |
| (kKlF)$_3$ + PSS | 66 | 34 |
| (kKlF)$_3$ + (EELF)$_3$(crosslinked) | 70 | 30 |

TABLE 19-continued

3-NOP release (%) from the PEC microcapsules. Samples are prepared with a 3-NOP concentration of 100 μM. Final pH solution ~7. K, L, F, and E refer to lysine, leucine, phenylalanine, and glutamic acid, respectively. PSS refers to polystyrene sulfonate.

| Polyelectrolyte Pair | Release (%) at 96 h timepoint | 3-NOP Concentration in Microcapsules (μM) |
|---|---|---|
| (kKlF)$_3$ + PSS (crosslinked) | 72 | 28 |

Figure 17:
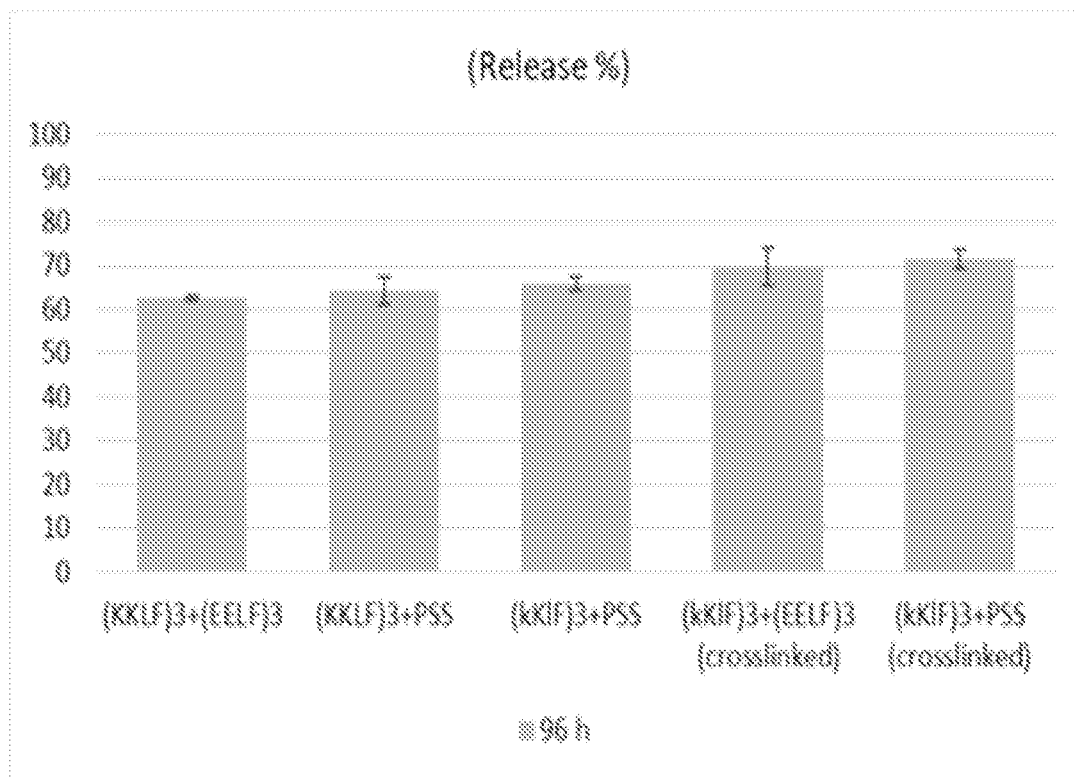
FIG. 17 is a bar graph showing 3-NOP release (%) from exemplary PEC microcapsules. Samples are prepared with a 3-NOP concentration of 100 μM. Final pH solution ~7. K, L, F, and E refer to lysine, leucine, phenylalanine, and glutamic acid, respectively. PSS refers to polystyrene sulfonate.

FIG. 17 is a graph showing 3-NOP release (%) from the PEC microcapsules. Samples are prepared with a 3-NOP concentration of 100 μM. Final pH solution ~7. K, L, F, and E refer to lysine, leucine, phenylalanine, and glutamic acid, respectively. PSS refers to polystyrene sulfonate.

Figure 18:
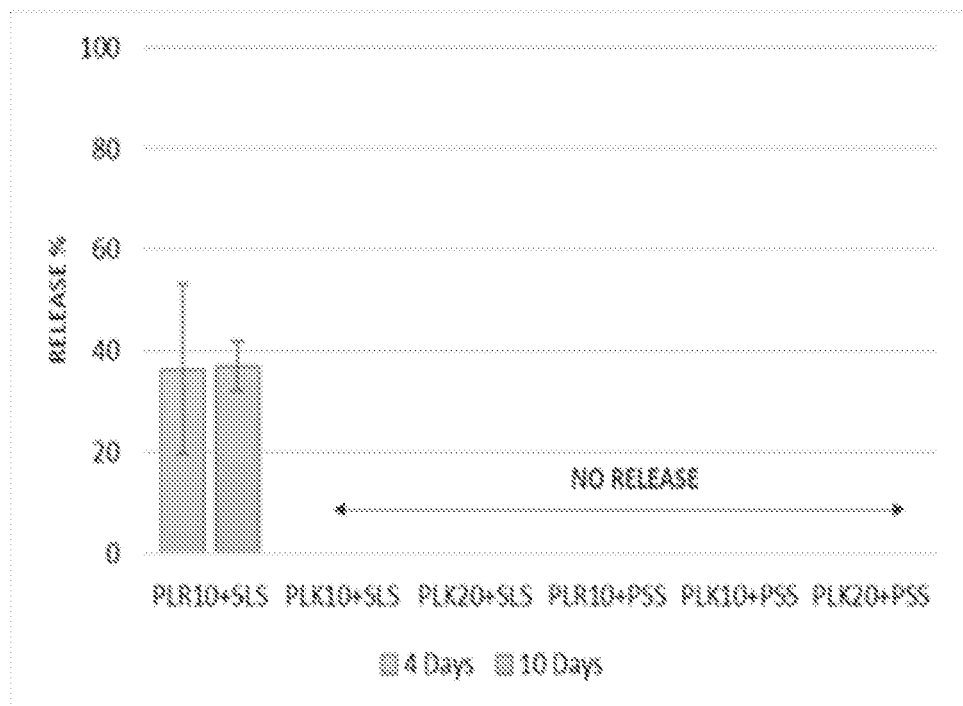
FIG. 18 is bar graph showing 3-NOP release (%) from exemplary PEC microcapsules. Samples are prepared with a 3-NOP concentration of 100 μM. Final pH solution ~7. PLR refers to poly (L-arginine), and PLK refers to poly (L-lysine). SLS and PSS refer to sodium lignosulfonate and polystyrene sulfonate.

Examples of release profiles of some microcapsules made of positively charged polypeptides with either polystyrene sulfonate (PSS) or sodium lignosulfonate (SLS) are shown in FIG. 18 (3-NOP release (%) from the PEC microcapsules. Samples are prepared with a 3-NOP concentration of 100 μM. Final pH solution ~7. PLR refers to poly (L-arginine), and PLK refers to poly (L-lysine). SLS and PSS refer to sodium lignosulfonate and polystyrene sulfonate).

The encapsulation efficiency of some PEC microcapsules prepared at neutral pH conditions is summarized in Table 20. Table 21 shows the encapsulation efficiency of samples prepared at pH~8.

TABLE 20

Encapsulation efficiency of the PEC microcapsules. Samples are prepared with a 3-NOP concentration of 100 μM. Final pH solution ~7. Upper and lower cases in (kKlF)3 sequences represent L and D-chirality, respectively.

| Polyelectrolyte Pair | Total Concentration (monomer charge basis) (mM) | Encapsulation Efficiency (%) | 3-NOP Concentration in Microcapsules (μM) |
|---|---|---|---|
| PLK20 + PRE20 | 5 | 7.4 | 7.4 |
| PLR10 + PRE20 | 5 | 0 | 0 |
| (KKLF)$_3$ + (EELF)$_3$ | 5 | 100 | 100 |
| (kKlF)$_3$ + (EELF)$_3$ | 5 | 22.2 | 22.2 |
| (KKLF)$_3$ + PSS | 5 | 37 | 37 |
| (kKlF)$_3$ + PSS | 5 | 100 | 100 |
| PAH + PSS | 5 | 30.9 | 30.9 |

TABLE 21

Encapsulation efficiency of the PEC microcapsules. Samples are prepared with a 3-NOP concentration of 2.5 mM. Final pH solution ~8. Upper and lower cases in (kKlF)3 sequences represent L and D-chirality of the amino acid residue, respectively.

| Polyelectrolyte Pair | Total Concentration (monomer charge basis) (mM) | Encapsulation Efficiency (%) | 3-NOP Concentration in Microcapsules (mM) |
|---|---|---|---|
| PLR10 + PRE20 | 5 | 50 | 1.25 |
| PLK20 + PRE20 | 5 | 53.8 | 1.34 |
| (kKlF)$_3$ + PRE20 | 5 | 50.2 | 1.26 |

Physical Crosslinking of 3-NOP With Small Molecules

3-NOP molecules can form hydrogen bonds with small molecules such as amino acids to make a larger size conjugate resulting in enhanced encapsulation efficiency. For example, an equal stoichiometry of 3-NOP and two selective amino acids, arginine and lysine, were reacted in aqueous solution for 24 h, and the solution was used for encapsulation studies. The results of such encapsulation with some PEC microcapsules are shown in Table 22.

TABLE 22

Encapsulation efficiency of the PEC microcapsules. Samples are prepared with a 3-NOP concentration of 125 μM. Final pH solution ~7.

| Polyelectrolyte Pair | Encapsulation Efficiency (%) | | 3-NOP Concentration in Microcapsules (μM) | |
|---|---|---|---|---|
| | Arginine-3-NOP | Lysine-3-NOP | Arginine-3-NOP | Lysine-3-NOP |
| PLR10 + PRE20 | 4.6 | 19.1 | 5.75 | 23.9 |
| PLK20 + PRE20 | 34.3 | 28.4 | 42.9 | 35.5 |
| (KKLF)$_3$ + (EELF)$_3$ | 27.4 | 34.8 | 34.25 | 43.5 |
| PAH + PAA | 30.3 | 47.1 | 37.9 | 58.9 |
| PAH + PSS | 67.4 | 67.6 | 84.3 | 84.5 |

VIII. Definitions

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The phrase "at least one" includes "one", "one or more", "one or a plurality" and "a plurality". The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A composition for reducing emissions of deleterious atmospheric gases and/or precursors thereof from a flooded ecosystem comprising:
one or more molecules that reduce production of one or more of the deleterious atmospheric gases and/or precursors thereof, wherein the one or more molecules comprise 3-nitrooxypropanol (3-NOP) and one or more agriculturally suitable solid carriers,
wherein the composition comprises particles, and
wherein the particles comprise a coating comprising two or more polyelectrolytes.

2. The composition of claim 1, wherein the one or more solid carriers comprises attapulgite, kaolinite, fuller's earth, calcium carbonate, perlite, diatomaceous earth, calcium silicate, fly ash, a polysaccharide, a disaccharide, a monosaccharide, a gum, silica, propylene glycol, hemp protein, biochar, montmorillonite, activated charcoal, lignin, wood flour, pea protein, soy protein, gelatin, casein, chitosan, talc, calcium phosphate, arginine, lysine, carbon black, glutamine, betaine, bismuth phosphate, bismuth citrate, iron phosphate, or any combination thereof.

3. The composition of claim 2, wherein the one or more solid carriers comprises a saccharide selected from cellulose, xanthan gum, karaya gum, ethylcellulose, inositol, galactose, arabinose, lactose, lactulose, mannitol, mannose, sorbose, turanose, platinose, carrageenan, cellulose acetate, hydroxypropyl cellulose, cellulose acteate phthalate, maltrodextran, dextran, inulin, corn starch, amylopectin, sodium starch glycolate, pentaerthritol, cyclodextrin, and any combination thereof.

4. The composition of claim 1 wherein the solid carrier comprises about 10% to about 50% by weight of silica and about 50 to about 90% by weight of ethylcelluose.

5. The composition of claim 1, wherein the carrier comprises about 10% to about 90% by weight of silica and about 10% to about 90% by weight of activated charcoal.

6. The composition of claim 1, wherein the carrier comprises about 10% to about 50% by weight of activated charcoal and about 40 to about 90% by weight of ethylcellulose.

7. The composition of claim 1, wherein the carrier comprises about 1 to about 10% by weight of sodium lignosulfate.

8. The composition of claim 1, wherein the carrier comprises about 10 to about 60% by weight of arginine and about 30 to about 90% by weight of polycaprolactone.

9. The composition of claim 1, wherein the carrier comprises about 10 to about 60% by weight of silica and about 30 to about 90% by weight of polycaprolactone.

10. The composition of claim 1, wherein the carrier comprises arginine, lysine, or both arginine and lysine.

11. The composition of claim 1, wherein the particles have a size ranging from about 1 mm to about 20 mm.

12. The composition of claim 1, wherein the coating comprises at least two layers.

13. The composition of claim 1, wherein the coating further comprises cellulose acetate phthalate, ethyl cellulose, hydroxypropyl cellulose, polycaprolactone, alginate, chitosan, polyethylene glycol, cellulose acetate, triacetin, propylene glycol, n-methyl-2-pyrollidone, or any combination thereof.

14. The composition of claim 1, wherein the polyelectrolytes comprise polystyrene sulfonate, polyethyleneimine, sodium lignosulfate, polyglutamic acid and poly-L-lysine, poly-L-arginine, polyallylamine hydrochloride, polyacrylic acid, or any combination thereof.

15. The composition of claim 14, wherein the polyelectrolytes comprise:

a) polyallylamine hydrochloride and sodium lignosulfate;
b) comprise polyallylamine hydrochloride and polystyrene sulfonate;
c) sodium lignosulfate and one of polyglutamic acid, poly-L-lysine, or poly-L-arginine, or
d) polystyrene sulfonate and one of polyglutamic acid, poly-L-lysine, or poly-L-arginine.

16. The composition of claim 15, wherein the two or more polyelectrolytes are chemically crosslinked.

17. The composition of claim 1, wherein the composition has a density of at least 1.1 g/mL.

18. The composition of claim 1, wherein about 40 to about 80% of the 3-NOP is thereof is released in a flooded ecosystem after 15 days.

19. The composition of claim 1, wherein the composition comprises about 1 to about 25% by weight of the 3-NOP.

20. A method for reducing emissions of deleterious atmospheric gases and/or precursors thereof from a flooded ecosystem comprising applying to the flooded ecosystem a composition comprising 3-NOP and one or more agriculturally suitable solid carriers,
wherein the composition comprises particles, and
wherein the particles comprise a coating comprising two or more polyelectrolytes.

21. The method of claim 20, further comprising reapplying the composition after a period of time.

22. The method of claim 21, wherein the period of time is from about 7 days to about 28 days.

23. The composition of claim 1, wherein the flooded ecosystem comprises a lagoon, wet meadow, marsh, swamp, peatland, mire, bog, fen, mangrove forest, carr, pocosin, floodplain, vernal pool, paddy field, or a suitable flooded agricultural field.

24. The method of claim 20, wherein the composition is applied to the flooded ecosystem aerially.

25. The method of claim 20, wherein the amount of the 3-NOP applied to the flooded ecosystem is from about 0.1 ppm to about 100 ppm per acre of flooded ecosystem.

* * * * *